US008227593B2

(12) United States Patent
Dobie et al.

(10) Patent No.: US 8,227,593 B2
(45) Date of Patent: Jul. 24, 2012

(54) MODULATION OF FORKHEAD BOX O1A EXPRESSION

(75) Inventors: Kenneth W. Dobie, Del Mar, CA (US); Sanjay Bhanot, Carlsbad, CA (US); Robert McKay, Poway, CA (US); Sanjay K. Pandey, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/860,137

(22) Filed: Aug. 20, 2010

(65) Prior Publication Data

US 2010/0311824 A1 Dec. 9, 2010

Related U.S. Application Data

(60) Division of application No. 11/739,017, filed on Apr. 23, 2007, now Pat. No. 7,807,649, which is a division of application No. 10/671,074, filed on Sep. 25, 2003, now Pat. No. 7,229,976, which is a continuation-in-part of application No. 10/260,203, filed on Sep. 26, 2002, now abandoned.

(51) Int. Cl.
*C07H 21/04* (2006.01)
(52) U.S. Cl. ............... 536/24.5; 536/24.31; 536/24.1; 435/6; 435/325; 435/375; 514/44
(58) Field of Classification Search ............... None
See application file for complete search history.

(56) References Cited

U.S. PATENT DOCUMENTS

| | | | |
|---|---|---|---|
| 5,576,302 A | 11/1996 | Cook et al. | |
| 5,650,278 A | 7/1997 | Barr et al. | |
| 5,670,317 A | 9/1997 | Ladanyi et al. | |
| 5,801,154 A | 9/1998 | Baracchini et al. | |
| 5,998,148 A | 12/1999 | Bennett et al. | |
| 6,329,203 B1* | 12/2001 | Bennett et al. | 435/377 |
| 6,410,325 B1* | 6/2002 | Bennett et al. | 435/375 |
| 6,582,908 B2 | 6/2003 | Fodor et al. | |
| 2001/0053519 A1 | 12/2001 | Fodor et al. | |
| 2002/0142305 A1 | 10/2002 | Chin et al. | |
| 2003/0096255 A1* | 5/2003 | Felix et al. | 435/6 |
| 2003/0228597 A1 | 12/2003 | Cowsert et al. | |
| 2005/0026164 A1 | 2/2005 | Zhou | |
| 2006/0003322 A1 | 1/2006 | Bentwich | |
| 2007/0031844 A1 | 2/2007 | Khvorova et al. | |
| 2007/0037144 A1* | 2/2007 | Wohlgemuth et al. | 435/6 |

FOREIGN PATENT DOCUMENTS

WO WO 94/01550 * 1/1994

OTHER PUBLICATIONS

Novina et al. Nature 2004; 430:161-164.*
Nikiforov et al. (PCR methods and applications 1994, vol. 3: 285-291).*
Myatt et al., "Definition of microRNAs That Repress Expression of the Tumor Suppressor Gene FOX01 in Endometrial Cancer" Cancer Res. (2010) 70(1):367-377.

European Search Report for application EP 10176027.0 dated Nov. 9, 2010.
Anderson et al., "Genes, chromosomes, and rhabdomyosarcoma", Genes. Chromosomes Cancer (1999) 26:275-285.
Anderson et al., "PAX3-FKHR induces morphological change and enhances cellular proliferation and invasion in rhabdomyosarcoma", Am. J. Pathol. (2001) 159:1089-1096.
Anderson et al., "Embryonic expression of the tumor-associated PAX3-FKHR fusion protein interferes with the developmental functions of PAX3", Proc. Natl. Acad. Sci. U.S.A. (2001) 98:1589-1594.
Anderson et al., GenBank Accession No. AF032885, 1998.
Bennicelli et al., "Mechanism for transcriptional gain of function resulting from chromosomal translocation in alveolar rhabdomyosarcoma", Proc. Natl. Acad. Sci. U.S.A. (1996) 93:5455-5459.
Bernasconi et al., "Induction of apoptosis in rhabdomyosarcoma cells through down-regulation of PAX proteins", Proc. Natl. Acad. Sci. U.S.A. (1996) 93:13164-13169.
Branch et al., "A good antisense molecule is hard to find," TIBS (1998)23:45-50.
Chin et al., "On the preparation of Utilization of Isolated and Purified Oligonucleotides", Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Davis et al., "Fusion genes resulting from alternative chromosomal translocations are overexpressed by gene-specific mechanisms in alveolar rhabdomyosarcoma", Proc. Natl. Acad. Sci. U.S.A. (1997) 94:8047-8051.
Davis et al., "Structural characterization of the FKHR gene and it's rearrangement in alveolar rhabdomyosarcoma", Hum. Mol. Genet. (1995) 4:2355-2362.
Davis et al., "Fusion of PAX7 to FKHR by the variant t(1;13)(p36;q14) translocation in alveolar rhabdomyosarcoma", Cancer Res. (1994) 54:2869-2872.
Del Peso et al., "Regulation of the forkhead transcription factor FKHR, but not the PAX3-FKHR fusion protein, by the serine/threonine kinase Akt", Oncogene (1999) 18:7328-7333.
Durham et al., "FKHR binds the insulin response element in the insulin-like growth factor binding protein-1 promoter", Endocrinology (1999) 140:3140-3146.
Epstein et al., "Tumor-specific PAX3-FKHR transcription factor, but not PAX3, activates the platelet-derived growth factor alpha receptor", Mol. Cell. Biol. (1998) 18:4118-4130.
Gajiwala et al., "Winged helix proteins", Curr. Opin. Struct. Biol. (2000) 10:110-116.
Galili et al., "Fusion of a fork head domain gene to PAX3 in the solid tumour alveolar rhabdomyosarcoma", Nat. Genet. (1993) 5:230-235.
Guo et al., "Phosphorylation of serine 256 by protein kinase B disrupts transactivation by FKHR and mediates effects of insulin on insulin-like growth factor-binding protein-1 promoter activity through a conserved insulin response sequence", J. Biol. Chem. (1999) 274:17184-17192.

(Continued)

*Primary Examiner* — Kimberly Chong
(74) *Attorney, Agent, or Firm* — Jones Day

(57) ABSTRACT

Antisense compounds, compositions and methods are provided for modulating the expression of forkhead box O1A. The compositions comprise antisense compounds, particularly antisense oligonucleotides, targeted to nucleic acids encoding forkhead box O1A. Methods of using these compounds for modulation of forkhead box O1A expression and for treatment of diseases associated with expression of forkhead box O1A are provided, in particular, for methods of treating diabetes.

19 Claims, 5 Drawing Sheets

OTHER PUBLICATIONS

Margue et al., "Transcriptional modulation of the anti-apoptotic protein BCL-XL by the paired box transcription factors PAX# and PAX3/FKHR", Oncogene (2000) 19:2921-2929.

Nakae et al., "The forkhead transcription factor Foxo1 (Fkhr) confers insulin sensitivity onto glucose-6-phosphatase expression", J. Clin. Invest. (2001) 108:1359-1367.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Scheidler et al., "The hybrid PAX3-FKHR fusion protein of alveolar rhabdomyosarcoma transforms fibroblasts in culture", Proc. Natl. Acad. Sci. U.S.A. (1996) 93:9805-9809.

Tang et al., "Negative regulation of the forkhead transcription factor FKHR by Akt", J. Biol. Chem. (1999) 274:16741-16746.

International Search Report dated Jan. 3, 2005 for application No. PCT/US03/30352.

Office Action for U.S. Appl. No. 10/671,074 dated Jan. 25, 2006.

Office Action for U.S. Appl. No. 10/671,074 dated Jun. 7, 2006.

Office Action for U.S. Appl. No. 11/739,017 dated Feb. 5, 2009.

Final Rejection for U.S. Appl. No. 11/739,017 dated Oct. 16, 2009.

* cited by examiner

SEQUENCE LISTING

<160> NUMBER OF SEQ ID NOS: 176

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                              20

<210> SEQ ID NO 4
<211> LENGTH: 5723
<212> TYPE: DNA
<213> ORGANISM: H. sapiens
<220> FEATURE:
<220> FEATURE:
<221> NAME/KEY: CDS
<222> LOCATION: (386)...(2353)

<400> SEQUENCE: 4
gcagccgcca cattcaacag gcagcagcgc agcgggcgcg ccgctgggga gagcaagcgg      60
cccgcggcgt ccgtccgtcc ttccgtccgc ggccctgtca gctggagcgc ggcgcaggct     120
ctgccccggc ccggcggctc tggccggccg tccagtccgt gcggcggacc ccgaggagcc     180

-continued

```
tcgatgtgga tggccccgcg aagttaagtt ctgggctcgc gcttccactc cgccgcgcct      240
tcctcccagt ttccgtccgc tcgccgcacc ggcttcgttc ccccaaatct cggaccgtcc      300
cttcgcgccc cctccccgtc cgccccccagt gctgcgttct cccccctcttg gctctcctgc   360 ggctggggga ggggcggggg tcacc atg gcc gag gcg cct cag gtg gtg gag       412
                            Met Ala Glu Ala Pro Gln Val Val Glu
                              1               5
```

| | | |
|---|---|---|
| atc gac ccg gac ttc gag ccg ctg ccc cgg ccg cgc tcg tgc acc tgg<br>Ile Asp Pro Asp Phe Glu Pro Leu Pro Arg Pro Arg Ser Cys Thr Trp<br>10              15              20              25 | | 460 |
| ccg ctg ccc agg ccg gag ttt agc cag tcc aac tcg gcc acc tcc agc<br>Pro Leu Pro Arg Pro Glu Phe Ser Gln Ser Asn Ser Ala Thr Ser Ser<br>          30              35              40 | | 508 |
| ccg gcg ccg tcg ggc agc gcg gct gcc aac ccc gac gcc gcg gcg ggc<br>Pro Ala Pro Ser Gly Ser Ala Ala Ala Asn Pro Asp Ala Ala Ala Gly<br>            45              50              55 | | 556 |
| ctg ccc tcg gcc tcg gct gcc gct gtc agc gcc gac ttc atg agc aac<br>Leu Pro Ser Ala Ser Ala Ala Ala Val Ser Ala Asp Phe Met Ser Asn<br>      60              65              70 | | 604 |
| ctg agc ttg ctg gag gag agc gag gac ttc ccg cag gcg ccc ggc tcc<br>Leu Ser Leu Leu Glu Glu Ser Glu Asp Phe Pro Gln Ala Pro Gly Ser<br>75              80              85 | | 652 |
| gtg gcg gcg gcg gtg gcg gcg gcg gcc gcg gcc gcc acc ggg ggg<br>Val Ala Ala Ala Val Ala Ala Ala Ala Ala Ala Ala Thr Gly Gly<br>90              95              100             105 | | 700 |
| ctg tgc ggg gac ttc cag ggc ccg gag gcg ggc tgc ctg cac cca gcg<br>Leu Cys Gly Asp Phe Gln Gly Pro Glu Ala Gly Cys Leu His Pro Ala<br>          110             115             120 | | 748 |
| cca ccg cag ccc ccg ccg ccc ggg ccg ctg tcg cag cac ccg ccg gtg<br>Pro Pro Gln Pro Pro Pro Pro Gly Pro Leu Ser Gln His Pro Pro Val<br>            125             130             135 | | 796 |
| ccc ccc gcc gcc gct ggg ccg ctc gcg ggg cag ccg cgc aag agc agc<br>Pro Pro Ala Ala Ala Gly Pro Leu Ala Gly Gln Pro Arg Lys Ser Ser<br>      140             145             150 | | 844 |
| tcg tcc cgc cgc aac gcg tgg ggc aac ctg tcc tac gcc gac ctc atc<br>Ser Ser Arg Arg Asn Ala Trp Gly Asn Leu Ser Tyr Ala Asp Leu Ile<br>155             160             165 | | 892 |
| acc aag gcc atc gag agc tcg gcg gag aag cgg ctc acg ctg tcg cag<br>Thr Lys Ala Ile Glu Ser Ser Ala Glu Lys Arg Leu Thr Leu Ser Gln<br>170             175             180             185 | | 940 |
| atc tac gag tgg atg gtc aag agc gtg ccc tac ttc aag gat aag ggt<br>Ile Tyr Glu Trp Met Val Lys Ser Val Pro Tyr Phe Lys Asp Lys Gly<br>          190             195             200 | | 988 |
| gac agc aac agc tcg gcg ggc tgg aag aat tca att cgt cat aat ctg<br>Asp Ser Asn Ser Ser Ala Gly Trp Lys Asn Ser Ile Arg His Asn Leu<br>            205             210             215 | | 1036 |
| tcc cta cac agc aag ttc att cgt gtg cag aat gaa gga act gga aaa<br>Ser Leu His Ser Lys Phe Ile Arg Val Gln Asn Glu Gly Thr Gly Lys<br>      220             225             230 | | 1084 |
| agt tct tgg tgg atg ctc aat cca gag ggt ggc aag agc ggg aaa tct<br>Ser Ser Trp Trp Met Leu Asn Pro Glu Gly Gly Lys Ser Gly Lys Ser<br>235             240             245 | | 1132 |
| cct agg aga aga gct gca tcc atg gac aac aac agt aaa ttt gct aag<br>Pro Arg Arg Arg Ala Ala Ser Met Asp Asn Asn Ser Lys Phe Ala Lys<br>250             255             260             265 | | 1180 |
| agc cga agc cga gct gcc aag aag aaa gca tct ctc cag tct ggc cag<br>Ser Arg Ser Arg Ala Ala Lys Lys Lys Ala Ser Leu Gln Ser Gly Gln<br>          270             275             280 | | 1228 |
| gag ggt gct ggg gac agc cct gga tca cag ttt tcc aaa tgg cct gca<br>Glu Gly Ala Gly Asp Ser Pro Gly Ser Gln Phe Ser Lys Trp Pro Ala | | 1276 |

```
                Glu Gly Ala Gly Asp Ser Pro Gly Ser Gln Phe Ser Lys Trp Pro Ala
                                285                 290                 295 agc cct ggc tct cac agc aat gat gac ttt gat aac tgg agt aca ttt         1324
Ser Pro Gly Ser His Ser Asn Asp Asp Phe Asp Asn Trp Ser Thr Phe
            300                 305                 310 cgc cct cga act agc tca aat gct agt act att agt ggg aga ctc tca         1372
Arg Pro Arg Thr Ser Ser Asn Ala Ser Thr Ile Ser Gly Arg Leu Ser
        315                 320                 325 ccc att atg acc gaa cag gat gat ctt gga gaa ggg gat gtg cat tct         1420
Pro Ile Met Thr Glu Gln Asp Asp Leu Gly Glu Gly Asp Val His Ser
330                 335                 340                 345 atg gtg tac ccg cca tct gcc gca aag atg gcc tct act tta ccc agt         1468
Met Val Tyr Pro Pro Ser Ala Ala Lys Met Ala Ser Thr Leu Pro Ser
                350                 355                 360 ctg tct gag ata agc aat ccc gaa aac atg gaa aat ctt ttg gat aat         1516
Leu Ser Glu Ile Ser Asn Pro Glu Asn Met Glu Asn Leu Leu Asp Asn
            365                 370                 375 ctc aac ctt ctc tca tca cca aca tca tta act gtt tcg acc cag tcc         1564
Leu Asn Leu Leu Ser Ser Pro Thr Ser Leu Thr Val Ser Thr Gln Ser
        380                 385                 390 tca cct ggc acc atg atg cag cag acg ccg tgc tac tcg ttt gcg cca         1612
Ser Pro Gly Thr Met Met Gln Gln Thr Pro Cys Tyr Ser Phe Ala Pro
395                 400                 405 cca aac acc agt ttg aat tca ccc agc cca aac tac caa aaa tat aca         1660
Pro Asn Thr Ser Leu Asn Ser Pro Ser Pro Asn Tyr Gln Lys Tyr Thr
410                 415                 420                 425 tat ggc caa tcc agc atg agc cct ttg ccc cag atg cct ata caa aca         1708
Tyr Gly Gln Ser Ser Met Ser Pro Leu Pro Gln Met Pro Ile Gln Thr
                430                 435                 440 ctt cag gac aat aag tcg agt tat gga ggt atg agt cag tat aac tgt         1756
Leu Gln Asp Asn Lys Ser Ser Tyr Gly Gly Met Ser Gln Tyr Asn Cys
            445                 450                 455 gcg cct gga ctc ttg aag gag ttg ctg act tct gac tct cct ccc cat         1804
Ala Pro Gly Leu Leu Lys Glu Leu Leu Thr Ser Asp Ser Pro Pro His
        460                 465                 470 aat gac att atg aca cca gtt gat cct ggg gta gcc cag ccc aac agc         1852
Asn Asp Ile Met Thr Pro Val Asp Pro Gly Val Ala Gln Pro Asn Ser
475                 480                 485 cgg gtt ctg ggc cag aac gtc atg atg ggc cct aat tcg gtc atg tca         1900
Arg Val Leu Gly Gln Asn Val Met Met Gly Pro Asn Ser Val Met Ser
490                 495                 500                 505 acc tat ggc agc cag gca tct cat aac aaa atg atg aat ccc agc tcc         1948
Thr Tyr Gly Ser Gln Ala Ser His Asn Lys Met Met Asn Pro Ser Ser
                510                 515                 520 cat acc cac cct gga cat gct cag cag aca tct gca gtt aac ggg cgt         1996
His Thr His Pro Gly His Ala Gln Gln Thr Ser Ala Val Asn Gly Arg
            525                 530                 535 ccc ctg ccc cac acg gta agc acc atg ccc cac acc tcg ggt atg aac         2044
Pro Leu Pro His Thr Val Ser Thr Met Pro His Thr Ser Gly Met Asn
        540                 545                 550 cgc ctg acc caa gtg aag aca cct gta caa gtg cct ctg ccc cac ccc         2092
Arg Leu Thr Gln Val Lys Thr Pro Val Gln Val Pro Leu Pro His Pro
555                 560                 565 atg cag atg agt gcc ctg ggg ggc tac tcc tcc gtg agc agc tgc aat         2140
Met Gln Met Ser Ala Leu Gly Gly Tyr Ser Ser Val Ser Ser Cys Asn
570                 575                 580                 585 ggc tat ggc aga atg ggc ctt ctc cac cag gag aag ctc cca agt gac         2188
Gly Tyr Gly Arg Met Gly Leu Leu His Gln Glu Lys Leu Pro Ser Asp
                590                 595                 600 ttg gat ggc atg ttc att gag cgc tta gac tgt gac atg gaa tcc atc         2236
```

```
                Leu Asp Gly Met Phe Ile Glu Arg Leu Asp Cys Asp Met Glu Ser Ile
                            605                 610                 615 att cgg aat gac ctc atg gat gga gat aca ttg gat ttt aac ttt gac                  2284
Ile Arg Asn Asp Leu Met Asp Gly Asp Thr Leu Asp Phe Asn Phe Asp
            620                 625                 630 aat gtg ttg ccc aac caa agc ttc cca cac agt gtc aag aca acg aca                  2332
Asn Val Leu Pro Asn Gln Ser Phe Pro His Ser Val Lys Thr Thr Thr
            635                 640                 645 cat agc tgg gtg tca ggc tga gggttagtga gcaggttaca cttaaaagta                     2383
His Ser Trp Val Ser Gly
650             655 cttcagattg tctgacagca ggaactgaga gaagcagtcc aaagatgtct ttcaccaact                2443
cccttttagt tttcttggtt aaaaaaaaaa acaaaaaaaa aaaccctcct ttttttcctt                2503
tcgtcagact tggcagcaaa gacatttttc ctgtacagga tgtttgccca atgtgtgcag                2563
gttatgtgct gctgtagata aggactgtgc cattggaaat tcattacaa tgaagtgcca                 2623 aactcactac accatataat tgcagaaaag attttcagat cctggtgtgc tttcaagttt                2683
tgtatataag cagtagatac agattgtatt tgtgtgtgtt tttggttttt ctaaatatcc                2743
aattggtcca aggaaagttt atactctttt tgtaatactg tgatgggcct catgtcttga                2803
taagttaaac ttttgtttgt actacctgtt ttctgcggaa ctgacggatc acaaagaact                2863
gaatctccat tctgcatctc cattgaacag ccttggacct gttcacgttg ccacagaatt                2923
cacatgagaa ccaagtagcc tgttatcaat ctgctaaatt aatggacttg ttaaactttt                2983
ggaaaaaaaa agattaaatg ccagcttgt acaggtcttt tctattttt tttgtttatt                  3043 ttgttatttg caaatttgta caaacattta atggttcta atttccagat aaatgatttt                 3103
tgatgttatt gttgggactt aagaacattt ttggaataga tattgaactg taataatgtt                3163
ttcttaaaac tagagtctac tttgttacat agtcagcttg taaattttgt ggaaccacag                3223
gtatttgggg cagcattcat aatttcatt ttgtattcta actggattag tactaatttt                 3283
atacatgctt aactggtttg tacactttgg gatgctactt agtgatgttt ctgactaatc                3343
ttaaatcatt gtaattagta cttgcatatt caacgtttca ggccctggtt gggcaggaaa                3403
gtgatgtata gttatggaca ctttgcgttt cttatttagg ataacttaat atgttttat                 3463 gtatgtattt taaagaaatt tcatctgctt ctactgaact atgcgtactg catagcatca                3523
agtcttctct agagacctct gtagtcctgg gaggcctcat aatgtttgta gatcagaaaa                3583
gggagatctg catctaaagc aatggtcctt tgtcaaacga gggattttga tccacttcac                3643
cattttgagt tgagctttag caaaagtttc ccctcataat tctttgctct tgtttcagtc                3703
caggtggagg ttggttttgt agttctgcct tgaggaatta tgtcaacact catacttcat                3763
ctcattctcc cttctgccct gcagattaga ttacttagca cactgtggaa gtttaagtgg                3823
aaggagggaa tttaaaaatg ggacttgagt ggtttgtaga atttgtgttc ataagttcag                3883
atgggtagca aatggaatag aacttactta aaaattgggg agatttattt gaaaccagc                 3943 tgtaagttgt gcattgagat tatgttaaaa gccttggctt aagaatttga aaatttcttt                4003
agcctgtagc aacctaaact gtaattccta tcattatgtt ttattacttt ccaattacct                4063
gtaactgaca gaccaaatta attggctttg tgtcctattt agtccatcag tattttcaag                4123 tcatgtgaa agcccaaagt catcacaatg aagagaacag gtgcacagca ctgttcctct                 4183
tgtgttcttg agaaggatct aatttttctg tatatagccc acatcacact tgctttgtct                4243
tgtatgttaa ttgcatcttc attggcttgg tatttcctaa atgttaaca agaacacaag                 4303 tgttcctgat aagatttcct acagtaagcc agctgtattg taagcttccc accgtgatga                4363
```

```
tcatttttt  gaagattcat  tgaacagcca  ccactctatc  atcctcattt  tggggcagtc    4423
caagacatag  ctggttttag  aaacccaagt  tcctctaagc  acagcctccc  gggtatgtaa    4483
ctgaacttgg  tgccaaagta  cttgtgtact  aatttctatt  actacgtact  gtcactttcc    4543
tcccgtgcca  ttactgcatc  ataatacaag  gaacctcaga  gcccccattt  gttcattaaa    4603
gaggcaacta  cagccaaaat  cactgttaaa  atcttactac  ttcatggagt  agctcttagg    4663
aaaatatatc  ttcctcctga  gtctgggtaa  ttatacctct  cccaagcccc  cattgtgtgt    4723
tgaaatcctg  tcatgaatcc  ttggtagctc  tctgagaaca  gtgaagtcca  gggaaaggca    4783
tctggtctgt  ctggaaagca  aacattatgt  ggcctctggt  agttttttc   ctgtaagaat    4843 actgactttc  tggagtaatg  agtatatatc  agttattgta  catgattgct  ttgtgaaatg    4903
tgcaaatgat  atcacctatg  cagccttgtt  tgatttattt  tctctggttt  gtactgttat    4963
taaaagcata  ttgtattata  gagctattca  gatattttaa  atataaagat  gtattgtttc    5023
cgtaatatag  acgtatggaa  tatatttagg  taatagatgt  attacttgga  aagttctgct    5083
ttgacaaact  gacaaagtct  aaatgagcac  atgtatccca  gtgagcagta  aatcaatgga    5143
acatcccaag  aagaggataa  ggatgcttaa  aatggaaatc  attctccaac  gatatacaaa    5203
ttggacttgt  tcaactgctg  gatatatgct  accaataacc  ccagcccaa   cttaaaattc    5263 ttacattcaa  gctcctaaga  gttcttaatt  tataactaat  tttaaagag   aagtttcttt    5323 tctggtttta  gtttgggaat  aatcattcat  taaaaaaat   gtattgtggt  ttatgcgaac    5383
agaccaacct  ggcattacag  ttggcctctc  cttgaggtgg  gcacagcctg  gcagtgtggc    5443
caggggtggc  catgtaagtc  ccatcaggac  gtagtcatgc  ctcctgcatt  tcgctacccg    5503
agtttagtaa  cagtgcagat  tccacgttct  tgttccgata  tctgagaag   tgcctgatgt    5563 tgatgtactt  acagacacaa  gaacaatctt  tgctataatt  gtataaagcc  ataaatgtac    5623
ataaattatg  tttaaatggc  ttggtgtctt  tcttttctaa  ttatgcagaa  taagctcttt    5683
attaggaatt  ttttgtgaag  ctattaaata  cttgagttaa                            5723
```

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
gcaatcccga aaacatggaa                                                     20

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
caggtgagga ctgggtcgaa                                                     20

<210> SEQ ID NO 7
<211> LENGTH: 34
<212> TYPE: DNA
<213> ORGANISM: Artificial Sequence
<220> FEATURE:
<223> OTHER INFORMATION: PCR Probe

<400> SEQUENCE: 7

-continued

```
tggataatct caaccttctc tcatcaccaa catc                                  34

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                  20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                  20

<210> SEQ ID NO 11
<211> LENGTH: 4945
<212> TYPE: DNA
<213> ORGANISM: M. musculus
<220> FEATURE:
<220> FEATURE:
<221> NAME/KEY: CDS
<222> LOCATION: (429)...(2387)

<400> SEQUENCE: 11
gcccgctgca gatcccgtaa gacgggagtc tgcggagtcg cttcagtccc cgccgccgcc      60
acattcaaca ggcagcagcg ccgctgtcgc gcggccgcgg agagctagag cggcccgcag     120
cgtccgcccg tctgccttgg cgtccgcggc ccttgtcagc gggagcgcgg tgcccgagct     180
gccgggctcc gcggcctggt cggtgccccg tcctaggcac gaactcggag gctccttaga     240
caccggtgac ccagcgaagt taagttctgg gcgcgtccgt ccgctgcgcc cgccgcgcc     300 tgactccggc gtgcgtccgc cgtccgcggc cccccaatct cggagcgaca ctcgggtcgc     360
ccgctccgcg cccccggtgg ccgcgtctcc cggtacttct ctgctggtgg gggaggggcg     420 ggggcacc atg gcc gaa gcg ccc cag gtg gtg gag acc gac ccg gac ttc      470
         Met Ala Glu Ala Pro Gln Val Val Glu Thr Asp Pro Asp Phe
           1               5                  10 gag ccg ctg ccc cgg cag cgc tcc tgt acc tgg ccg ctg ccc agg ccg      518
Glu Pro Leu Pro Arg Gln Arg Ser Cys Thr Trp Pro Leu Pro Arg Pro
 15                  20                  25                  30 gag ttt aac cag tcc aac tcg acc acc tcc agt ccg gcg ccg tcg ggc      566
Glu Phe Asn Gln Ser Asn Ser Thr Thr Ser Ser Pro Ala Pro Ser Gly
                 35                  40                  45 ggc gcg gcc gcc aac ccc gac gcc gcg gcg agc ctg gcc tcg gcg tcc      614
Gly Ala Ala Ala Asn Pro Asp Ala Ala Ala Ser Leu Ala Ser Ala Ser
             50                  55                  60
```

```
gct gtc agc acc gac ttt atg agc aac ctg agc ctg ctg gag gag agt      662
Ala Val Ser Thr Asp Phe Met Ser Asn Leu Ser Leu Leu Glu Glu Ser
             65                  70                  75 gag gac ttc gcg cgg gcg cca ggc tgc gtg gcc gtg gcg gcg gcg gct      710
Glu Asp Phe Ala Arg Ala Pro Gly Cys Val Ala Val Ala Ala Ala Ala
         80                  85                  90 gcg gcc agc agg ggc ctg tgc ggg gac ttc cag ggc ccc gag gcg ggc      758
Ala Ala Ser Arg Gly Leu Cys Gly Asp Phe Gln Gly Pro Glu Ala Gly
 95                 100                 105                 110 tgc gtg cac cca gcg ccg cca cag ccc cca ccg acc ggg ccg ctg tcg      806
Cys Val His Pro Ala Pro Pro Gln Pro Pro Pro Thr Gly Pro Leu Ser
                115                 120                 125 cag ccc cca ccc gtg cct ccc tcc gct gcc gcc gcg ggg cca ctc          854
Gln Pro Pro Pro Val Pro Pro Ser Ala Ala Ala Ala Gly Pro Leu
            130                 135                 140 gcg gga cag ccg cgc aag acc agc tcg tcg cgc cgc aac gcg tgg ggc      902
Ala Gly Gln Pro Arg Lys Thr Ser Ser Ser Arg Arg Asn Ala Trp Gly
        145                 150                 155 aac ctg tcg tac gcc gac ctc atc acc aag gcc atc gag agc tca gcc      950
Asn Leu Ser Tyr Ala Asp Leu Ile Thr Lys Ala Ile Glu Ser Ser Ala
    160                 165                 170 gag aag agg ctc acc ctg tcg cag atc tac gag tgg atg gtg aag agc      998
Glu Lys Arg Leu Thr Leu Ser Gln Ile Tyr Glu Trp Met Val Lys Ser
175                 180                 185                 190 gtg ccc tac ttc aag gat aag ggc gac agc aac agc tcg gcg ggc tgg     1046
Val Pro Tyr Phe Lys Asp Lys Gly Asp Ser Asn Ser Ser Ala Gly Trp
                195                 200                 205 aag aat tca att cgc cac aat ctg tcc ctt cac agc aag ttt att cga     1094
Lys Asn Ser Ile Arg His Asn Leu Ser Leu His Ser Lys Phe Ile Arg
            210                 215                 220 gtg cag aat gaa gga act gga aag agt tct tgg tgg atg ctc aat cca     1142
Val Gln Asn Glu Gly Thr Gly Lys Ser Ser Trp Trp Met Leu Asn Pro
        225                 230                 235 gag gga ggc aag agc gga aaa tca ccc cgg aga aga gct gcg tcc atg     1190
Glu Gly Gly Lys Ser Gly Lys Ser Pro Arg Arg Arg Ala Ala Ser Met
    240                 245                 250 gac aac aac agt aaa ttt gct aag agc cga ggg cgg gct gct aag aaa     1238
Asp Asn Asn Ser Lys Phe Ala Lys Ser Arg Gly Arg Ala Ala Lys Lys
255                 260                 265                 270 aaa gca tct ctc cag tct ggg caa gag ggt cct gga gac agc cct ggg     1286
Lys Ala Ser Leu Gln Ser Gly Gln Glu Gly Pro Gly Asp Ser Pro Gly
                275                 280                 285 tct cag ttt tct aag tgg cct gcg agt cct ggg tcc cac agc aac gat     1334
Ser Gln Phe Ser Lys Trp Pro Ala Ser Pro Gly Ser His Ser Asn Asp
            290                 295                 300 gac ttt gat aac tgg agt aca ttc cgt cct cga acc agc tca aat gct     1382
Asp Phe Asp Asn Trp Ser Thr Phe Arg Pro Arg Thr Ser Ser Asn Ala
        305                 310                 315 agt acc atc agt ggg aga ctt tct ccc atc atg aca gag cag gat gac     1430
Ser Thr Ile Ser Gly Arg Leu Ser Pro Ile Met Thr Glu Gln Asp Asp
    320                 325                 330 ctg gga gat ggg gac gtg cat tcc ctg gtg tat cca ccc tct gct gcc     1478
Leu Gly Asp Gly Asp Val His Ser Leu Val Tyr Pro Pro Ser Ala Ala
335                 340                 345                 350 aag atg gcg tct acg ctg ccc agt ctg tct gaa atc agc aat cca gaa     1526
Lys Met Ala Ser Thr Leu Pro Ser Leu Ser Glu Ile Ser Asn Pro Glu
                355                 360                 365 aac atg gag aac ctt ctg gat aat ctc aac ctt ctc tcg tcc cca aca     1574
Asn Met Glu Asn Leu Leu Asp Asn Leu Asn Leu Leu Ser Ser Pro Thr
            370                 375                 380
```

| | |
|---|---|
| tct tta act gtg tcc acc cag tcc tcg cct ggc agc atg atg cag cag<br>Ser Leu Thr Val Ser Thr Gln Ser Ser Pro Gly Ser Met Met Gln Gln<br>385 390 395 | 1622 |
| aca cca tgc tat tcg ttt gca ccg cca aac acc agt cta aat tca ccc<br>Thr Pro Cys Tyr Ser Phe Ala Pro Pro Asn Thr Ser Leu Asn Ser Pro<br>400 405 410 | 1670 |
| agt cca aac tac tca aag tac aca tac ggc caa tcc agc atg agc cct<br>Ser Pro Asn Tyr Ser Lys Tyr Thr Tyr Gly Gln Ser Ser Met Ser Pro<br>415 420 425 430 | 1718 |
| ttg ccc cag atg cct atg cag aca ctt cag gac agc aaa tca agt tac<br>Leu Pro Gln Met Pro Met Gln Thr Leu Gln Asp Ser Lys Ser Ser Tyr<br>435 440 445 | 1766 |
| gga gga ttg aac cag tat aac tgt gcc cca gga ctc ttg aaa gag ttg<br>Gly Gly Leu Asn Gln Tyr Asn Cys Ala Pro Gly Leu Leu Lys Glu Leu<br>450 455 460 | 1814 |
| ttg act tct gac tct cct ccc cac aat gac att atg tca ccg gtt gat<br>Leu Thr Ser Asp Ser Pro Pro His Asn Asp Ile Met Ser Pro Val Asp<br>465 470 475 | 1862 |
| ccc gga gtg gcc caa ccc aac agt cgg gtc ctg ggc caa aat gta atg<br>Pro Gly Val Ala Gln Pro Asn Ser Arg Val Leu Gly Gln Asn Val Met<br>480 485 490 | 1910 |
| atg ggc cct aat tcg gtc atg cca gcg tat ggc agc cag gca tct cat<br>Met Gly Pro Asn Ser Val Met Pro Ala Tyr Gly Ser Gln Ala Ser His<br>495 500 505 510 | 1958 |
| aac aaa atg atg aac ccc agc tcc cac acc cac cct gga cat gca cag<br>Asn Lys Met Met Asn Pro Ser Ser His Thr His Pro Gly His Ala Gln<br>515 520 525 | 2006 |
| caa acg gct tcg gtc aac ggc cgt acc ctg ccc cat gtg gtg aac acc<br>Gln Thr Ala Ser Val Asn Gly Arg Thr Leu Pro His Val Val Asn Thr<br>530 535 540 | 2054 |
| atg cct cac aca tct gcc atg aac cgc ttg acc ccc gtg aag aca cct<br>Met Pro His Thr Ser Ala Met Asn Arg Leu Thr Pro Val Lys Thr Pro<br>545 550 555 | 2102 |
| tta caa gtg cct ctg tcc cac ccc atg cag atg agt gcc ctg ggc agc<br>Leu Gln Val Pro Leu Ser His Pro Met Gln Met Ser Ala Leu Gly Ser<br>560 565 570 | 2150 |
| tac tcc tcg gtg agc agc tgc aat ggc tat ggt agg atg ggt gtc ctc<br>Tyr Ser Ser Val Ser Ser Cys Asn Gly Tyr Gly Arg Met Gly Val Leu<br>575 580 585 590 | 2198 |
| cac cag gag aag ctc cca agt gac ttg gat ggc atg ttt att gag cgc<br>His Gln Glu Lys Leu Pro Ser Asp Leu Asp Gly Met Phe Ile Glu Arg<br>595 600 605 | 2246 |
| ttg gac tgt gac atg gag tcc atc att cgg aat gac ctc atg gat gga<br>Leu Asp Cys Asp Met Glu Ser Ile Ile Arg Asn Asp Leu Met Asp Gly<br>610 615 620 | 2294 |
| gat acc ttg gat ttt aac ttt gat aat gtg ttg ccc aac caa agc ttc<br>Asp Thr Leu Asp Phe Asn Phe Asp Asn Val Leu Pro Asn Gln Ser Phe<br>625 630 635 | 2342 |
| cca cac agt gtc aag act aca aca cac agc tgg gtg tca ggc taa<br>Pro His Ser Val Lys Thr Thr Thr His Ser Trp Val Ser Gly<br>640 645 650 | 2387 |
| gagttagtga gcaggctaca tttaaaagtc cttcagattg tctgacagca ggaactgagg | 2447 |
| agcagtccaa agatgccctt caccctcct tatagttttc aagatttaaa aaaaaaaaa | 2507 |
| aaaaaaaaaa aagtccttc tcctttcctc agacttggca acagcggcag cactttcctg | 2567 |
| tgcaggatgt ttgcccagcg tccgcaggtt ttgtgctcct gtagataagg actgtgccat | 2627 |
| tgggaatcat tacaatgaag tgccaaactc actacaccat gtaattgcag aaaagacttt | 2687 |
| cagatcctgg agtgctttca gtttttgtat atatgcagta gatacagaat tgtatttgtg | 2747 |

```
tgtgtgtttt ttaatacccta cttggtccaa ggaaagttta tactcttttg taatactgtg    2807
atggtctcaa gtcttgataa actttgcttt gtactacctg tgttctgcta cagtgagaag    2867
tcatgaacta agatctctgt cctgcacctc ggctgaatga ctgaacctgg tcatttgcca    2927
cagaacccat gagagccaag tagccagtga tcaatgtgct gaattaatgg acttgtcaaa    2987
ctttggggca gaataagatt aagtgccagc tttgtacagg tcttttttcta ttgttttttgt    3047
tgttgtttat tttgttattt gcaaatttgt acaaacaact taaaatggtt ctaatttcca    3107
gataaatgac ttttgatgtt attgttagga ctcaacatct tttggaatag ataccgaagt    3167
gtaatgtttt cttaaaacta gagtctactt tgttacattg tctgcttata aatttgtgaa    3227
atcagaggta tttgggggct gcattcataa ttttcatttt gtatttctaa ctggattagt    3287
actaatttta tatgtgctca gctggtttgt acactttgcg atgatacctg ataatgtttc    3347
tgactaatcg taaaccattg taattagtac ttgcacactc aacgttcctg gcccttttggg    3407
caggaaagtt atgtatagtt acagacactc tgttttgtgt gtagatttat gtgtgtattt    3467
taaagaaatt tcacctgctt ttattaccct gtgagttgtg tacagcgcat agcaccaagt    3527
cttcagatag atgccacgtg cttacagcct tctaggaag cctgccagat gatgccctgt    3587
gtcacgctgt catagttccc atgggaactc tgtctgtcgc tcaggaaagg ggaacttttta    3647
tctaaggtga tgttctttgt ctgactgggg ttcgcctcct actactctga gctgttggct    3707
tttgtcacga tggaggtggc tttgtggctc tgtcctggaa gaatcctgtc acttctcggt    3767
ccccacctct gttctctttg gctctgaaca gtgtaaatct aaggaggaag tttacaaata    3827
ggacttcagt gatttatgga gtgctctgtg cgcctaagta cagacagtgg caggattagt    3887
taaaaatgaa ggcagtaaac ttggaaacca gccagctata aatggacatt tattttgaaa    3947
tccttagctt aagaatttga gaagtttttt cagccttgag cagcctaatg tgtctcaaac    4007
atttacgttt tttatacatt ctatttacct gaaatcctgc cagaccagga taattggttt    4067
tacctctcat tccgtccatc ggtgtttccc agtctcccac agtttgagga atagatgtac    4127
cccagcaccc ctctttgcct ttatgagaag gcctggtttg catgagaaga ccaaattgca    4187
cttccatgag aagaccaaat tgtttgtagt gttacttagc tctcccctcg tttgttagtg    4247
tgtgttaaca agaataaaat gtccctgctt tcacccaccg ttggccagct ttgtcatagg    4307
cttcccacca taactttcac tattttaaac acatattgag ccactgctcg tctgactacc    4367
tttgtttggg cactccaaaa caggacttgt tttagaaatg aactcctcca agtagagcct    4427
ccttcaaaca gagtagaatt tcctggtgtc aaagaacccg ggtctgtctc cctttcctcc    4487
tccctctgcc atttcttacc attgcggaaa gagagagcct ccgtgtgtaa tcattcagta    4547
gaggcagcta ccgccctggc agtggtctac ctgctgaatg ccactgaatg actaggaggt    4607
gtctctccct tcagaagctg tcaatttcag cagcaacccc tgttttcctt ggtgttaaga    4667
tcccagtgtg aatcatgggc agttgtctgg ggcacagtga actccaggaa aggcttcgta    4727
tctgttttga aaacaaacat caaacgtgtg agctccgagg gtccttttct gggagaatgt    4787
tcgctttctg gtctattatt gtacatgatt gctctgtgaa aagacttcat ctatgcagcc    4847
ttgtttgatt catttccttt ggtgtgttct gttgttaaga gcaaattgta ttatagagct    4907
atttggatat tttaaatata aagatgtatt gtttccat                           4945

<210> SEQ ID NO 12
<211> LENGTH: 23
<212> TYPE: DNA
<213> ORGANISM: Artificial Sequence
```

```
<220> FEATURE:
<223> OTHER INFORMATION: PCR Primer

<400> SEQUENCE: 12
caaagtacac atacggccaa tcc                                           23

<210> SEQ ID NO 13
<211> LENGTH: 24
<212> TYPE: DNA
<213> ORGANISM: Artificial Sequence
<220> FEATURE:
<223> OTHER INFORMATION: PCR Primer

<400> SEQUENCE: 13
cgtaacttga tttgctgtcc tgaa                                          24

<210> SEQ ID NO 14
<211> LENGTH: 25
<212> TYPE: DNA
<213> ORGANISM: Artificial Sequence
<220> FEATURE:
<223> OTHER INFORMATION: PCR Probe

<400> SEQUENCE: 14
tgagcccttt gccccagatg cctat                                         25

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                               20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                               20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                       27

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tgcctgttga atgtggcggc                                               20
```

```
<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ccggcctggg cagcggccag                                                 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ccctggaagt ccccgcacag                                                 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttggtgatga ggtcggcgta                                                 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
tctcgatggc cttggtgatg                                                 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ttgaagtagg gcacgctctt                                                 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctctggattg agcatccacc                                                 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
```
aaatttactg ttgttgtcca                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cttagcaaat ttactgttgt                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ccagactgga gagatgcttt                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
aatgtactcc agttatcaaa                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
agagaaggtt gagattatcc                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gggctcatgc tggattggcc                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gggaggagag tcagaagtca                                              20

<210> SEQ ID NO 32
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 32
tgagatgcct ggctgccata                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
atcattttgt tatgagatgc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cagggcactc atctgcatgg                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tagccattgc agctgctcac                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gggagcttct cctggtggag                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
catccaagtc acttgggagc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
aggtcattcc gaatgatgga                                              20
```

```
<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gtatctccat ccatgaggtc                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ctttggttgg gcaacacatt                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ggaagctttg gttgggcaac                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tgacactgtg tgggaagctt                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tgctgtcaga caatctgaag                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ggcacagtcc ttatctacag                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
```
ttggcacttc attgtaatga                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ggtgtagtga gtttggcact                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
aaagagtata aactttcctt                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tgtacaaatt tgcaaataac                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
catttatctg gaaattagaa                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tagactctag ttttaagaaa                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
atgtaacaaa gtagactcta                                               20

<210> SEQ ID NO 52
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 52
taaaattagt actaatccag                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tgaaatttct ttaaaataca                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aatcaaacaa ggctgcatag                                              20

<210> SEQ ID NO 55
<211> LENGTH: 528
<212> TYPE: DNA
<213> ORGANISM: M. musculus
<220> FEATURE:

<400> SEQUENCE: 55
ggtgtgttct gttgttaaga gcaaattgta ttatagagct atttggatat tttaaatata    60
aagatgtatt gtttccataa tatagatgta tggagtatat ttaggtgata gatgtacaac   120
ttggaaagtt ctgcttggac aaactgagtc taagttaatt agcaaataat atatcctgat   180
gagcaggaag ccctgaaacc taacaacagt aagcggagaa aatcacttaa aatggaaaca   240
gttccccaaa ggtgttcaat ttgaacttgt tcaactgctt aatatatggt ccccccccc   300 cccaaaaaaa aaaccttgaa gttcttagtt ttcagctctc caagttactg attttaagtg   360
aagtttctct gtggtttcag ctggggagtg attgttcagt agagtgtgca ttgtgctttta   420 tgcaaaccaa acagcctggc cctgtggccg gggacagaca gacagcccgt caggatagag   480
tcccgccctt cgccaccaca gcggacttga gtaacagtgc agatgcct                528

<210> SEQ ID NO 56
<211> LENGTH: 391
<212> TYPE: DNA
<213> ORGANISM: M. musculus
<220> FEATURE:

<400> SEQUENCE: 56
gttcaactgc ttaatatttg tcccccccc ccccaaaaaa aaaaccttga agttcttagt     60
tttcagctcc ccaagttact gattttaagt gaagttctct gtggtttcag ctggggagtg   120
attgttcagt agagtgtgca ttgtgcttta tgcaaaccaa acagcactgc cctgtggccg   180
gggacagaca gacagcccgt caggatagag tcccgccctt cgccaccaca gcggacttga   240
gtaacagtgc agatgccttg ctcctgttcc attgctatct gagaagtgcc tgatgaggat   300
ggtaaactta cagacacaag aacaatcctt actgtgcgtt gtataaagcc ataaatgtac   360
ataaatcctc caaaaaaaaa aaaaaaaaa a                                  391
```

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ctcccgtctt acgggatctg                                         20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cgctgctgcc tgttgaatgt                                         20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tgtctaagga gcctccgagt                                         20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
cagagaagta ccgggagacg                                         20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cttcggccat ggtgcccccg                                         20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
taaactccgg cctgggcagc                                         20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
caggttgccc cacgcgttgc                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tggccttggt gatgaggtcg                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ggtgagcctc ttctcggctg                                           20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tccagttcct tcattctgca                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tcggctctta gcaaatttac                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctccagttat caaagtcatc                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
acagactggg cagcgtagac                                           20

<210> SEQ ID NO 70
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 70
ggcaaagggc tcatgctgga                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
accgaattag ggcccatcat                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ttgttatgag atgcctggct                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tcacttggga gcttctcctg                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
acatgccatc caagtcactt                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tccatgaggt cattccgaat                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tgtgtgggaa gctttggttg                                              20
```

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
cactaactct tagcctgaca                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
agttcctgct gtcagacaat                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ccaatggcac agtccttatc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gtgagtttgg cacttcattg                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ataaactttc cttggaccaa                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
agacctgtac aaagctggca                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 83
tctggaaatt agaaccattt                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ctagttttaa gaaaacatta                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
acaaagtaga ctctagtttt                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tagtactaat ccagttagaa                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tgcaagtact aattacaatg                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tggtgctatg cgctgtacac                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
agctggctgg tttccaagtt                                               20

<210> SEQ ID NO 90
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 90
ggccttctca taaaggcaaa                                                20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
agttcactgt gccccagaca                                                20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gaaacaatac atctttatat                                                20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gactcagttt gtccaagcag                                                20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gtttggtttg cataaagcac                                                20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
gggccaggct gtttggtttg                                                20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
ggcacttctc agatagcaat                                                20
```

```
<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gaggatttat gtacatttat                                              20

<210> SEQ ID NO 98
<211> LENGTH: 20
<212> TYPE: DNA
<213> ORGANISM: H. sapiens
<220> FEATURE:

<400> SEQUENCE: 98
gccgccacat tcaacaggca                                              20

<210> SEQ ID NO 99
<211> LENGTH: 20
<212> TYPE: DNA
<213> ORGANISM: H. sapiens
<220> FEATURE:

<400> SEQUENCE: 99
ctggccgctg cccaggccgg                                              20

<210> SEQ ID NO 100
<211> LENGTH: 20
<212> TYPE: DNA
<213> ORGANISM: H. sapiens
<220> FEATURE:

<400> SEQUENCE: 100
ctgtgcgggg acttccaggg                                              20

<210> SEQ ID NO 101
<211> LENGTH: 20
<212> TYPE: DNA
<213> ORGANISM: H. sapiens
<220> FEATURE:

<400> SEQUENCE: 101
tacgccgacc tcatcaccaa                                              20

<210> SEQ ID NO 102
<211> LENGTH: 20
<212> TYPE: DNA
<213> ORGANISM: H. sapiens
<220> FEATURE:

<400> SEQUENCE: 102
catcaccaag gccatcgaga                                              20

<210> SEQ ID NO 103
<211> LENGTH: 20
<212> TYPE: DNA
<213> ORGANISM: H. sapiens
<220> FEATURE:

<400> SEQUENCE: 103
aagagcgtgc cctacttcaa                                              20
```

```
<210> SEQ ID NO 104
<211> LENGTH: 20
<212> TYPE: DNA
<213> ORGANISM: H. sapiens
<220> FEATURE:

<400> SEQUENCE: 104
ggtggatgct caatccagag                                              20

<210> SEQ ID NO 105
<211> LENGTH: 20
<212> TYPE: DNA
<213> ORGANISM: H. sapiens
<220> FEATURE:

<400> SEQUENCE: 105
tggacaacaa cagtaaattt                                              20

<210> SEQ ID NO 106
<211> LENGTH: 20
<212> TYPE: DNA
<213> ORGANISM: H. sapiens
<220> FEATURE:

<400> SEQUENCE: 106
acaacagtaa atttgctaag                                              20

<210> SEQ ID NO 107
<211> LENGTH: 20
<212> TYPE: DNA
<213> ORGANISM: H. sapiens
<220> FEATURE:

<400> SEQUENCE: 107
aaagcatctc tccagtctgg                                              20

<210> SEQ ID NO 108
<211> LENGTH: 20
<212> TYPE: DNA
<213> ORGANISM: H. sapiens
<220> FEATURE:

<400> SEQUENCE: 108
tttgataact ggagtacatt                                              20

<210> SEQ ID NO 109
<211> LENGTH: 20
<212> TYPE: DNA
<213> ORGANISM: H. sapiens
<220> FEATURE:

<400> SEQUENCE: 109
ggataatctc aaccttctct                                              20

<210> SEQ ID NO 110
<211> LENGTH: 20
<212> TYPE: DNA
<213> ORGANISM: H. sapiens
<220> FEATURE:

<400> SEQUENCE: 110
ggccaatcca gcatgagccc                                              20

<210> SEQ ID NO 111
<211> LENGTH: 20
<212> TYPE: DNA
```

<213> ORGANISM: H. sapiens
<220> FEATURE:

<400> SEQUENCE: 111
tatggcagcc aggcatctca                                           20

<210> SEQ ID NO 112
<211> LENGTH: 20
<212> TYPE: DNA
<213> ORGANISM: H. sapiens
<220> FEATURE:

<400> SEQUENCE: 112
gcatctcata acaaaatgat                                           20

<210> SEQ ID NO 113
<211> LENGTH: 20
<212> TYPE: DNA
<213> ORGANISM: H. sapiens
<220> FEATURE:

<400> SEQUENCE: 113
ccatgcagat gagtgccctg                                           20

<210> SEQ ID NO 114
<211> LENGTH: 20
<212> TYPE: DNA
<213> ORGANISM: H. sapiens
<220> FEATURE:

<400> SEQUENCE: 114
gtgagcagct gcaatggcta                                           20

<210> SEQ ID NO 115
<211> LENGTH: 20
<212> TYPE: DNA
<213> ORGANISM: H. sapiens
<220> FEATURE:

<400> SEQUENCE: 115
gctcccaagt gacttggatg                                           20

<210> SEQ ID NO 116
<211> LENGTH: 20
<212> TYPE: DNA
<213> ORGANISM: H. sapiens
<220> FEATURE:

<400> SEQUENCE: 116
tccatcattc ggaatgacct                                           20

<210> SEQ ID NO 117
<211> LENGTH: 20
<212> TYPE: DNA
<213> ORGANISM: H. sapiens
<220> FEATURE:

<400> SEQUENCE: 117
gacctcatgg atggagatac                                           20

<210> SEQ ID NO 118
<211> LENGTH: 20
<212> TYPE: DNA
<213> ORGANISM: H. sapiens
<220> FEATURE:

```
<400> SEQUENCE: 118
aatgtgttgc ccaaccaaag                                              20

<210> SEQ ID NO 119
<211> LENGTH: 20
<212> TYPE: DNA
<213> ORGANISM: H. sapiens
<220> FEATURE:

<400> SEQUENCE: 119
gttgcccaac caaagcttcc                                              20

<210> SEQ ID NO 120
<211> LENGTH: 20
<212> TYPE: DNA
<213> ORGANISM: H. sapiens
<220> FEATURE:

<400> SEQUENCE: 120
aagcttccca cacagtgtca                                              20

<210> SEQ ID NO 121
<211> LENGTH: 20
<212> TYPE: DNA
<213> ORGANISM: H. sapiens
<220> FEATURE:

<400> SEQUENCE: 121
cttcagattg tctgacagca                                              20

<210> SEQ ID NO 122
<211> LENGTH: 20
<212> TYPE: DNA
<213> ORGANISM: H. sapiens
<220> FEATURE:

<400> SEQUENCE: 122
ctgtagataa ggactgtgcc                                              20

<210> SEQ ID NO 123
<211> LENGTH: 20
<212> TYPE: DNA
<213> ORGANISM: H. sapiens
<220> FEATURE:

<400> SEQUENCE: 123
tcattacaat gaagtgccaa                                              20

<210> SEQ ID NO 124
<211> LENGTH: 20
<212> TYPE: DNA
<213> ORGANISM: H. sapiens
<220> FEATURE:

<400> SEQUENCE: 124
agtgccaaac tcactacacc                                              20

<210> SEQ ID NO 125
<211> LENGTH: 20
<212> TYPE: DNA
<213> ORGANISM: H. sapiens
<220> FEATURE:

<400> SEQUENCE: 125
aaggaaagtt tatactcttt                                              20
```

```
<210> SEQ ID NO 126
<211> LENGTH: 20
<212> TYPE: DNA
<213> ORGANISM: H. sapiens
<220> FEATURE:

<400> SEQUENCE: 126
gttatttgca aatttgtaca                                               20

<210> SEQ ID NO 127
<211> LENGTH: 20
<212> TYPE: DNA
<213> ORGANISM: H. sapiens
<220> FEATURE:

<400> SEQUENCE: 127
tagagtctac tttgttacat                                               20

<210> SEQ ID NO 128
<211> LENGTH: 20
<212> TYPE: DNA
<213> ORGANISM: H. sapiens
<220> FEATURE:

<400> SEQUENCE: 128
ctggattagt actaatttta                                               20

<210> SEQ ID NO 129
<211> LENGTH: 20
<212> TYPE: DNA
<213> ORGANISM: H. sapiens
<220> FEATURE:

<400> SEQUENCE: 129
ctatgcagcc ttgtttgatt                                               20

<210> SEQ ID NO 130
<211> LENGTH: 20
<212> TYPE: DNA
<213> ORGANISM: M. musculus
<220> FEATURE:

<400> SEQUENCE: 130
actcggaggc tccttagaca                                               20

<210> SEQ ID NO 131
<211> LENGTH: 20
<212> TYPE: DNA
<213> ORGANISM: M. musculus
<220> FEATURE:

<400> SEQUENCE: 131
cgtctcccgg tacttctctg                                               20

<210> SEQ ID NO 132
<211> LENGTH: 20
<212> TYPE: DNA
<213> ORGANISM: M. musculus
<220> FEATURE:

<400> SEQUENCE: 132 cggggggcacc atggccgaag                                              20

<210> SEQ ID NO 133
```

-continued

```
<211> LENGTH: 20
<212> TYPE: DNA
<213> ORGANISM: M. musculus
<220> FEATURE:

<400> SEQUENCE: 133
gctgcccagg ccggagttta                                              20

<210> SEQ ID NO 134
<211> LENGTH: 20
<212> TYPE: DNA
<213> ORGANISM: M. musculus
<220> FEATURE:

<400> SEQUENCE: 134
gcaacgcgtg gggcaacctg                                              20

<210> SEQ ID NO 135
<211> LENGTH: 20
<212> TYPE: DNA
<213> ORGANISM: M. musculus
<220> FEATURE:

<400> SEQUENCE: 135
cagccgagaa gaggctcacc                                              20

<210> SEQ ID NO 136
<211> LENGTH: 20
<212> TYPE: DNA
<213> ORGANISM: M. musculus
<220> FEATURE:

<400> SEQUENCE: 136
tgcagaatga aggaactgga                                              20

<210> SEQ ID NO 137
<211> LENGTH: 20
<212> TYPE: DNA
<213> ORGANISM: M. musculus
<220> FEATURE:

<400> SEQUENCE: 137
gatgactttg ataactggag                                              20

<210> SEQ ID NO 138
<211> LENGTH: 20
<212> TYPE: DNA
<213> ORGANISM: M. musculus
<220> FEATURE:

<400> SEQUENCE: 138
gtctacgctg cccagtctgt                                              20

<210> SEQ ID NO 139
<211> LENGTH: 20
<212> TYPE: DNA
<213> ORGANISM: M. musculus
<220> FEATURE:

<400> SEQUENCE: 139
tccagcatga gccctttgcc                                              20

<210> SEQ ID NO 140
<211> LENGTH: 20
<212> TYPE: DNA
<213> ORGANISM: M. musculus
```

```
<220> FEATURE:

<400> SEQUENCE: 140
atgatgggcc ctaattcggt                                               20

<210> SEQ ID NO 141
<211> LENGTH: 20
<212> TYPE: DNA
<213> ORGANISM: M. musculus
<220> FEATURE:

<400> SEQUENCE: 141
agccaggcat ctcataacaa                                               20

<210> SEQ ID NO 142
<211> LENGTH: 20
<212> TYPE: DNA
<213> ORGANISM: M. musculus
<220> FEATURE:

<400> SEQUENCE: 142
caggagaagc tcccaagtga                                               20

<210> SEQ ID NO 143
<211> LENGTH: 20
<212> TYPE: DNA
<213> ORGANISM: M. musculus
<220> FEATURE:

<400> SEQUENCE: 143
attcggaatg acctcatgga                                               20

<210> SEQ ID NO 144
<211> LENGTH: 20
<212> TYPE: DNA
<213> ORGANISM: M. musculus
<220> FEATURE:

<400> SEQUENCE: 144
caaccaaagc ttcccacaca                                               20

<210> SEQ ID NO 145
<211> LENGTH: 20
<212> TYPE: DNA
<213> ORGANISM: M. musculus
<220> FEATURE:

<400> SEQUENCE: 145
tgtcaggcta agagttagtg                                               20

<210> SEQ ID NO 146
<211> LENGTH: 20
<212> TYPE: DNA
<213> ORGANISM: M. musculus
<220> FEATURE:

<400> SEQUENCE: 146
attgtctgac agcaggaact                                               20

<210> SEQ ID NO 147
<211> LENGTH: 20
<212> TYPE: DNA
<213> ORGANISM: M. musculus
<220> FEATURE:

<400> SEQUENCE: 147
```
gataaggact gtgccattgg                                          20

<210> SEQ ID NO 148
<211> LENGTH: 20
<212> TYPE: DNA
<213> ORGANISM: M. musculus
<220> FEATURE:

<400> SEQUENCE: 148
caatgaagtg ccaaactcac                                          20

<210> SEQ ID NO 149
<211> LENGTH: 20
<212> TYPE: DNA
<213> ORGANISM: M. musculus
<220> FEATURE:

<400> SEQUENCE: 149
ttggtccaag gaaagtttat                                          20

<210> SEQ ID NO 150
<211> LENGTH: 20
<212> TYPE: DNA
<213> ORGANISM: M. musculus
<220> FEATURE:

<400> SEQUENCE: 150
tgccagcttt gtacaggtct                                          20

<210> SEQ ID NO 151
<211> LENGTH: 20
<212> TYPE: DNA
<213> ORGANISM: M. musculus
<220> FEATURE:

<400> SEQUENCE: 151
aaatggttct aatttccaga                                          20

<210> SEQ ID NO 152
<211> LENGTH: 20
<212> TYPE: DNA
<213> ORGANISM: M. musculus
<220> FEATURE:

<400> SEQUENCE: 152
gtgtacagcg catagcacca                                          20

<210> SEQ ID NO 153
<211> LENGTH: 20
<212> TYPE: DNA
<213> ORGANISM: M. musculus
<220> FEATURE:

<400> SEQUENCE: 153
aacttggaaa ccagccagct                                          20

<210> SEQ ID NO 154
<211> LENGTH: 20
<212> TYPE: DNA
<213> ORGANISM: M. musculus
<220> FEATURE:

<400> SEQUENCE: 154
tttgccttta tgagaaggcc                                          20

```
<210> SEQ ID NO 155
<211> LENGTH: 20
<212> TYPE: DNA
<213> ORGANISM: M. musculus
<220> FEATURE:

<400> SEQUENCE: 155
tgtctggggc acagtgaact                                                     20

<210> SEQ ID NO 156
<211> LENGTH: 20
<212> TYPE: DNA
<213> ORGANISM: M. musculus
<220> FEATURE:

<400> SEQUENCE: 156
ctgcttggac aaactgagtc                                                     20

<210> SEQ ID NO 157
<211> LENGTH: 20
<212> TYPE: DNA
<213> ORGANISM: M. musculus
<220> FEATURE:

<400> SEQUENCE: 157
gtgctttatg caaaccaaac                                                     20

<210> SEQ ID NO 158
<211> LENGTH: 20
<212> TYPE: DNA
<213> ORGANISM: M. musculus
<220> FEATURE:

<400> SEQUENCE: 158
attgctatct gagaagtgcc                                                     20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
tgccccacgc gttgcggcgg                                                     20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
ggcaacgtga acaggtccaa                                                     20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
agctgactat gtaacaaagt                                                     20
```

```
<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
aactgtgatc cagggctgtc                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
cccagggcac tcatctgcat                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
ctaagcgctc aatgaacatg                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
tagcagattg ataacaggct                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
ggctgggtga attcaaactg                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
catgaccgaa ttagggccca                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 168
cattccgaat gatggattcc                                               20

<210> SEQ ID NO 169
<211> LENGTH: 19
<212> TYPE: RNA
<213> ORGANISM: Artificial Sequence
<220> FEATURE:
<223> OTHER INFORMATION: Antisense Oligonucleotide

<400> SEQUENCE: 169
cgagaggcgg acgggaccg                                                19

<210> SEQ ID NO 170
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: Misc_feature
<222> LOCATION: 1-19
<223> OTHER INFORMATION: bases at these positions are RNA

<400> SEQUENCE: 170
cgagaggcgg acgggaccgt t                                             21

<210> SEQ ID NO 171
<211> LENGTH: 21
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: Misc_feature
<222> LOCATION: 1, 2, 3, 5, 6, 7, 8, 10,
      11, 12, 13, 14, 16, 18, 19
<223> OTHER INFORMATION: bases at these positions are RNA

<400> SEQUENCE: 171
cggtcccgtc cgcctctcgt t                                             21

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
gctttggttg ggcaacacat                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
ccgcttctcc gccgagctct                                               20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 174
ccgccagggc actcatctgc                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
tgcttctctc agttcctgct                                              20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
catagaatgc acatcccctt                                              20
```

MODULATION OF FORKHEAD BOX O1A EXPRESSION

CROSS-REFERENCE TO RELATED APPLICATIONS

This application is a divisional of U.S. application Ser. No. 11/739,017 filed Apr. 23, 2007, allowed Jun. 2, 2010, which is a divisional of U.S. application Ser. No. 10/671,074 filed Sep. 25, 2003, issued as U.S. Pat. No. 7,229,976 on Jun. 12, 2007, which is a continuation-in-part of U.S. application Ser. No. 10/260,203 filed Sep. 26, 2002, now abandoned, each of which is incorporated herein by reference in its entirety.

SEQUENCE LISTING

The present application is being filed along with a Sequence Listing in electronic format. The Sequence Listing is provided as a file entitled HTS0008USD2SEQ.txt, created on Aug. 17, 2010 which is 57 Kb in size. The information in the electronic format of the sequence listing is incorporated herein by reference in its entirety.

FIELD OF THE INVENTION

The present invention provides compositions and methods for modulating the expression of forkhead box 01A. In particular, this invention relates to compounds, particularly oligonucleotide compounds which, in some embodiments, hybridize with nucleic acid molecules encoding forkhead box 01A. Such compounds are shown herein to modulate the expression of forkhead box 01A.

BACKGROUND OF THE INVENTION

The forkhead gene family, originally identified in *Drosophila*, encodes a class of transcription factors that are important for embryogenesis and development. The forkhead domain, also referred to as the "winged helix domain", is a 100 amino acid sequence which forms a variation of a helix-turn-helix such that the target DNA is recognized by an alpha-helix and two large loops or "wings". The action of transcription factors is essential for proper development since vertebrate development relies on appropriate temporal and spatial expression of genes. Consequently, errors in the action of forkhead transcription factors may help to identify the molecular basis for developmental defects (Gajiwala and Burley, Curro Opin. Struct. Biol., 2000, 10, 110-116).

One of these forkhead genes, forkhead box 01A (also called FOX01A, forkhead in rhabdomyosarcoma, forkhead box 01A (rhabdomyosarcoma), forkhead (*drosophila*) homolog 1, FKHR, FKH1, FKHR/PAX3 fusion gene, and FKHR/PAX7 fusion gene) was identified and cloned in 1993 based on a chromosomal translocation that is frequently found to be overexpressed or amplified in a high proportion of alveolar rhabdomyosarcomas (ARMS) (Davis and Barr, Proc. Natl. Acad. Sci. U.S.A., 1997, 94, 8047-8051; Davis et al., Cancer Res., 1994, 54, 2869-2872; Galili et al., Nat. Genet., 1993, 5, 230-235). Rhabdomyosarcomas are a group of malignant tumors which are the most common soft-tissue sarcoma of childhood, and ARMS is associated with the expression of two fusion proteins: one is a fusion of the transcription factor PAX3 to forkhead box 01A and the second is a fusion of the transcription factor PAX7 to forkhead box 01A. These fusion genes arise from the chromosomal translocation of the gene encoding the transcription factor PAX3, located on chromosome 2, or PAX7 located on chromosome 1, to a position on chromosome 13 adjacent to the forkhead box 01A gene. Intron 1 of the forkhead box 01A gene is rearranged in t(2; 13)-containing alveolar rhabdomyosarcomas (Davis et al., Hum. Mol. Genet., 1995, 4, 2355-2362). The fusion protein resulting from the t(2; 13) translocation contains the N-terminal region of PAX3, including the DNA-binding domains, and the C-terminal transcription activation domain of forkhead box O1A, with truncation of the forkhead DNA-binding domain (Anderson et al., Genes. Chromosomes Cancer, 1999, 26, 275-285).

Diabetes and its complications are a serious problem for the populations of industrialized countries. Generally, this disease results from impaired insulin production from pancreatic β-cells. In type 2 diabetes, a combination of genetic and environmental factors brings about β-cell failure, which results in impaired insulin secretion and activity. In contrast, an autoimmune process destroys β-cells in type 1 diabetes. Since most individuals with type 2 diabetes are insulin resistant, it is commonly thought that the β-cells failure observed in individuals with type 2 diabetes is related to insulin resistance.

The forkhead box O1A protein may play a role in the progression of diabetes as well as several other diseases. Forkhead box O1A is the transcription factor that binds the insulin response element in the insulin-like growth factor binding protein-1 (IGF-BP-1) promoter (Durham et al., Endocrinology, 1999, 140, 3140-3146). It has been observed that insulin also regulates the activity of forkhead box O1A as a transcription factor of glucose-6-phosphatase, a key enzyme in gluconeogenesis (Nakae et al., J. Clin. Invest., 2001, 108, 1359-1367). Nakae et al. showed that Foxo1 controls two important processes in the pathogenesis of type 2 diabetes: hepatic glucose production and β-cell compensation of insulin resistance. The data suggest a common mechanism by which insulin resistance would bring about metabolic alterations that cause type 2 diabetes. Furthermore, Guo et al. (J. Biol. Chem., 1999, 274, 17184-17192) determined that forkhead box O1A stimulates promoter activity through an insulin response sequence. In addition, Guo et al., using a mutant forkhead box O1A, in which phosphorylation sites were mutated to prevent phosphorylation, showed that phosphorylation of forkhead box O1A by protein kinase B is necessary in order for insulin to disrupt transcription of target genes by forkhead box O1A. It has further been shown that forkhead box O1A activity, but not the PAX3/forkhead box O1A fusion protein activity, can also be suppressed by phosphorylation by Akt (del Peso et al., Oncogene, 1999, 18, 7328-7333; Tang et al., J. Biol. Chem., 1999, 274, 16741-16746). From these observations, it appears that forkhead box O1A may contribute to hepatic production of IGFBP-1 and unrestrained gluconeogenesis in Type 2 diabetes because insulin is not able to regulate the activity of forkhead box O1 as a transcription factor of IGFBP-1.

Prior to the present invention, there were no known therapeutic agents that effectively inhibited the synthesis of forkhead box O1A.

The present invention provides compositions and methods for modulating forkhead box O1A expression.

SUMMARY OF THE INVENTION

The present invention is directed to compounds, particularly nucleic acid and nucleic acid-like oligomers, which are targeted to a nucleic acid encoding forkhead box O1A, and which modulate the expression of forkhead box O1A. Pharmaceutical and other compositions comprising the compounds of the invention are also provided. Also provided are methods of screening for modulators of forkhead box O1A and methods of modulating the expression of forkhead box O1A in cells, tissues, or animals comprising contacting the cells, tissues, or animals with one or more of the compounds or compositions of the invention. Methods of treating an animal, particularly a human, suspected of having or being prone to a disease or condition associated with expression of forkhead box O1A are also set forth herein. In particular, the compounds of the present invention are effective for treating diabetes, in particular type 2 diabetes. Such methods comprise administering a therapeutically or prophylactically effective amount of one or more of the compounds or compositions of the invention to the animal or human in need of treatment.

DESCRIPTION OF EMBODIMENTS

Figure 1:
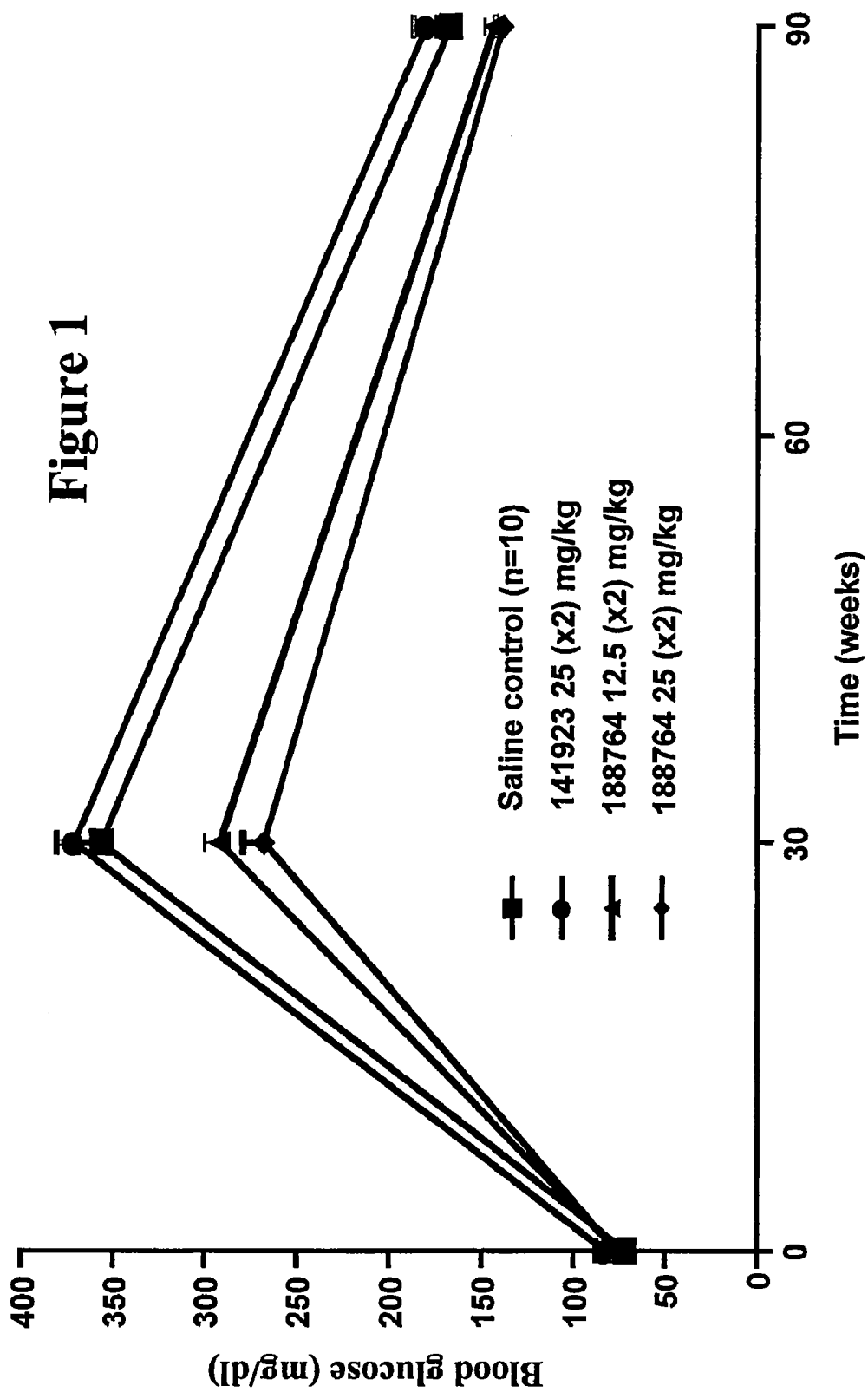
FIG. 1 shows the effects of an antisense compound in a glucose tolerance test in lean C57B16 mice. Compound 188764 significantly improved glucose tolerance tests in these animals.

The present invention employs compounds, such as oligonucleotides and similar species for use in modulating the function or effect of nucleic acid molecules encoding forkhead box O1A. In particular, the present invention provides compounds that are effective in treating diabetes, in particular type 2 diabetes, as is demonstrated in the Examples below.

The present invention demonstrates that reducing forkhead levels is an effective method for treating diabetes in a subject, particularly type 2 diabetes. The present invention also demonstrates that reducing forkhead levels is an effective method for decreasing blood or plasma glucose, improving glucose tolerance, and normalizing insulin levels. Any of the compounds or compositions described herein can be administered to a subject, such as a human, in an amount effective to reduce forkhead levels. Adminsitration of compounds and/or compositions can be carried out as described below. Such an amount can depend on, for example, the species of animal, weight, height, age, sex, stage of disease or condition, and the like. Forkhead box O1A expression can be measured and/or monitored by any of the methods described herein. The subjects can be previously diagnosed with diabetes or can be susceptible to developing diabetes or at high risk of developing diabetes.

Forkhead box O1A controls two important processes in the pathogenesis of type 2 diabetes: hepatic glucose production and β-cell compensation of insulin resistance. Forkhead box O1A has also been demonstrated to stimulate promoter activity through an insulin response sequence. Indeed, phosphorylation of forkhead box O1A by protein kinase B is necessary for insulin to disrupt transcription of target genes by forkhead box O1A. Thus, it appears that forkhead box O1A may contribute to hepatic production of IGFBP-1 and unrestrained gluconeogenesis in Type 2 diabetes because insulin is not able to regulate the activity of forkhead box O1 as a transcription factor of IGFBP-1.

The present invention employs compounds, such as oligonucleotides and similar species for use in modulating the function or effect of nucleic acid molecules encoding forkhead box O1A, which can be useful in preventing or treating a hyperproliferative disorder, such as cancer, particularly, rhabdomyosarcoma. Expression of the PAX3/forkhead box O1A fusion protein is able to induce phenotypic changes, including transforming fibroblasts in culture (Scheidler et al., Proc. Natl. Acad. Sci. U.S.A., 1996, 93, 9805-9809) and inducing the morphological features of ARMS in vivo (Anderson et al., Am. J. Pathol., 2001, 159, 1089-1096). The PAX3/forkhead box O1A fusion protein confers upon embryonal rhabdomyosarcoma cells protection from apoptosis, a key feature of tumorigenicity, at least in part by transcriptional regulation of the anti-apoptotic protein BCL-XL (Bemasconi et al., Proc. Natl. Acad. Sci. U.S.A., 1996, 93, 13164-13169; Margue et al., Oncogene, 2000, 19, 2921-2929). The PAX3/forkhead box O1A fusion protein transcribes genes normally transcribed by PAX3 and may even transcribe genes that are not targets of PAX3, as is the case with the platelet-derived growth factor alpha receptor promoter (Epstein et al., Mol. Cell. Biol., 1998, 18, 4118-4130). The PAX3/forkhead box O1A fusion protein is a more potent transcriptional activator than the normal PAX3 protein, and it has been suggested that this upregulation of genes that are normally targets of PAX3 could be a critical event in the histology of ARMS (Bennicelli et al., Proc. Natl. Acad. Sci. U.S.A., 1996, 93, 5455-5459). Expression of the PAX3/forkhead box O1A fusion protein may also interfere with normal developmental functions of PAX3 as evidenced in transgenic mice (Anderson et al., Proc. Natl. Acad. Sci. U.S.A., 2001, 98, 1589-1594).

The present invention provides compounds that reduce the level of both human and murine forkhead box O1A. In addition, the compounds described herein can also reduce the level of monkey forkhead box O1A. This is demonstrated by both in vitro and in vivo assays as set forth in the Examples below. In addition, it is shown that reducing forkhead levels has beneficial effects on various animal models of diabetes, normalizing glucose intolerance and insulin levels, and decreasing blood glucose levels. This is accomplished by providing oligonucleotides or other oligomeric compounds that specifically hybridize with one or more nucleic acid molecules encoding forkhead box O1A. As used herein, the terms "target nucleic acid" and "nucleic acid molecule encoding forkhead box O1A" have been used for convenience to encompass DNA encoding forkhead box O1A, RNA (including pre-mRNA and mRNA, or portions thereof) transcribed from such DNA, and also cDNA derived from such RNA. The hybridization of a compound of this invention with its target nucleic acid is generally referred to as "antisense". Consequently, a mechanism believed to be included in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, specific nucleic acid molecules and their functions for such antisense inhibition are targeted.

Functions of DNA to be interfered with can include, but are not limited to, replication and transcription. Replication and transcription, for example, can be from an endogenous cellular template, a vector, a plasmid construct or otherwise. The functions of RNA to be interfered with can include, but are not limited to, functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of forkhead box O1A. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is one form of modulation of expression and mRNA is often a target nucleic acid.

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays. Of course, the compounds of the invention need not be specifically hybridizable to modulate the expression of forkhead box O1A. Indeed, in some embodiments, the compounds of the invention are hybridizable to nucleic acid molecules encoding forkhead box O1A. In other embodiments, the compounds are specifically hybridizable to nucleic acid molecules encoding forkhead box O1A.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligomer or oligonucleotide may hybridize over one or more segments such that intervening or adjacent segments are not involved in the hybridization event (e.g., a loop structure or hairpin structure). In some embodiments, the compounds of the present invention comprise at least 70%, or at least 75%, or at least 80%, at least 85%, at least 90%, at least 95%, or at least 99% sequence complementarity to a target region within the target nucleic acid. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases that are flanked by two regions of complete complementarity with the target nucleic acid would have 77.8% overall complementarity with the target nucleic acid and would fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, that uses the algorithm of Smith and Waterman (Adv. Appl. Math., 1981, 2, 482-489). In some embodiments, homology, sequence identity or complementarity, between the oligomeric and target is between about 50% to about 60%. In some embodiments, homology, sequence identity or complementarity, is between about 60% to about 70%. In other embodiments, homology, sequence identity or complementarity, is between about 70% and about 80%. In other embodiments, homology, sequence identity or complementarity, is between about 80% and about 90%. In other embodiments, homology, sequence identity or complementarity, is about 90%, about 92%, about 94%, about 95%, about 96%, about 97%, about 98%, or about 99%.

According to the present invention, compounds include, but are not limited to, antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, Cell, 1995, 81, 611-620). Montgomery et al. have shown that the primary interference effects of dsRNA are posttranscriptional (Montgomery et al., Proc. Natl. Acad. Sci. USA, 1998, 95, 15502-15507).

The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). Recently, it has been shown that it is, in fact, the single-stranded RNA oligomers of antisense polarity of the dsRNAs which are the potent inducers of RNAi (Tijsterman et al., Science, 2002, 295, 694-697).

The oligonucleotides and oligomers of the present invention also include variants in which a different base is present at one or more of the nucleotide positions in the oligonucleotide or oligomer. For example, if the first nucleotide is an adenosine, variants may be produced which contain thymidine, guanosine or cytidine at this position. This may be done at any of the positions of the oligonucleotide. These oligonucleotides are then tested using the methods described herein to determine their ability to inhibit expression of forkhead box O1A mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions that function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are one form of the compounds of this invention, the present invention comprehends other families of compounds as well, including but not limited to, oligonucleotide analogs and mimetics such as those described herein.

The compounds in accordance with this invention comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Antisense compounds 8 to 80 nucleobases in length comprising a stretch of at least eight (8) consecutive nucleobases selected from within the illustrative antisense compounds are considered to be suitable antisense compounds as well.

Exemplary antisense compounds include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly, antisense compounds can be represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the antisense compounds illustrated herein will be able, without undue experimentation, to identify additional antisense compounds.

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes forkhead box O1A.

The targeting process usually also includes determination of at least one target region, segment, or site within the target nucleic acid for the antisense interaction to occur such that a desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules;

5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding forkhead box O1A, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region can also be targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also target sites. mRNA transcripts produced via the process of splicing of two (or more) mRNAs from different gene sources are known as "fusion transcripts." It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant produces a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also target nucleic acids.

The locations on the target nucleic acid to which the antisense compounds hybridize are hereinbelow referred to as "target segments." As used herein, the term "target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain target segments are set forth herein, one of skill in the art will recognize that these serve to illustrate and describe particular embodiments within the scope of the present invention. Additional target segments may be identified by one having ordinary skill.

Target segments 8-80 nucleobases in length comprising a stretch of at least eight (8) consecutive nucleobases selected from within the illustrative target segments are considered to be suitable for targeting as well.

Target segments can include DNA or RNA sequences that comprise at least the 8 consecutive nucleobases from the 5'-terminus of one of the illustrative target segments (the remaining nucleobases being a consecutive stretch of the same DNA or RNA beginning immediately upstream of the 5'-terminus of the target segment and continuing until the DNA or RNA contains about 8 to about 80 nucleobases). Similarly target segments are represented by DNA or RNA sequences that comprise at least the 8 consecutive nucleobases from the 3'-terminus of one of the illustrative target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the target segments illustrated herein will be able, without undue experimentation, to identify additional target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds are also targeted to or not targeted to regions of the target nucleobase sequence (e.g., such as those disclosed in Example 13) comprising nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2300, 2301-2350, 2351-2400, 2401-2450, 2451-2500, 2501-2550, 2551-2600, 2601-2650, 2651-2700, 2701-2750, 2751-2800, 2801-2850, 2851-2900, 2901-2950, 2951-3000, 3001-3050, 3051-3100, 3101-3150, 3151-3200, 3201-3250, 3251-3300, 3301-3350, 3351-3400, 3401-3450, 3451-3500, 3501-3550, 3551-3600, 3601-3650, 3751-3700, 3701-3750, 3751-3800, 3801-3850, 3851-3900, 3901-3950, 3951-4000, 4001-4050, 4051-4100, 4101-4150, 4151-4200, 4201-4250, 4251-4300, 4301-4350, 4351-4400, 4401-4450, 4451-4500, 4501-4550, 4551-4600, 4601-4650, 4751-4700, 4701-4750, or 4751-4800, 4801-4850, 4851-4900, 4901-4950, 4951-5000, 5001-5050, 5051-5100, 5101-5150, 5151-5200, 5201-5250, 5251-5300, 5301-5350, 5351-5400, 5401-5450, 5451-5500, 5501-5550, 5551-5600, 5601-5650, 5751-5700, 5701-5723, or any combination thereof.

In a further embodiment, the "target segments" identified herein may be employed in a screen for additional compounds that modulate the expression of forkhead box O1A. "Modulators" are those compounds that decrease or increase the expression of a nucleic acid molecule encoding forkhead box O1A and which comprise at least an 8-nucleobase portion which is complementary to a target segment. The screening method comprises the steps of contacting a target segment of a nucleic acid molecule encoding forkhead box O1A with one or more candidate modulators, and selecting for one or more candidate modulators which decrease or increase the expression of a nucleic acid molecule encoding forkhead box O1A. Once it is shown that the candidate modulator or modulators are capable of modulating (e.g. either decreasing or increasing) the expression of a nucleic acid molecule encoding forkhead box O1A, the modulator may then be employed in further investigative studies of the function of forkhead box O1A, or for use as a research, diagnostic, or therapeutic agent in accordance with the present invention.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The compounds of the present invention can also be applied in the areas of drug discovery and target validation. The present invention comprehends the use of the compounds and target segments identified herein in drug discovery efforts to elucidate relationships that exist between forkhead box O1A and a disease state, phenotype, or condition. These methods include detecting or modulating forkhead box O1A comprising contacting a sample, tissue, cell, or organism with the compounds of the present invention, measuring the nucleic acid or protein level of forkhead box O1A and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Cana, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The compounds of the invention are also useful for research and diagnostics because, for example, these compounds hybridize to nucleic acids encoding forkhead box O1A. For example, oligonucleotides that are shown to hybridize with such efficiency and under such conditions as disclosed herein as to be effective forkhead box O1A inhibitors will also be effective primers or probes under conditions favoring gene amplification or detection, respectively. These primers and probes are useful in methods requiring the specific detection of nucleic acid molecules encoding forkhead box O1A and in the amplification of the nucleic acid molecules for detection or for use in further studies of forkhead box O1A. Hybridization of the antisense oligonucleotides, particularly the primers and probes, of the invention with a nucleic acid encoding forkhead box O1A can be detected by means known in the art. Such means may include conjugation of an enzyme to the oligonucleotide, radiolabelling of the oligonucleotide or any other suitable detection means. Kits using such detection means for detecting the level of forkhead box O1A in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues, and animals, especially humans.

For therapeutics, an animal, such as a human, suspected of having a disease or disorder which can be treated by modulating the expression of forkhead box O1A, is treated by administering antisense compounds in accordance with this invention. For example, in one non-limiting embodiment, the methods comprise the step of administering to the animal in need of treatment, a therapeutically effective amount of a forkhead box O1A inhibitor. The forkhead box O1A inhibitors of the present invention effectively inhibit the activity of the forkhead box O1A protein or inhibit the expression of the forkhead box O1A protein. In one embodiment, the activity or expression of forkhead box O1A in an animal is inhibited or decreased by about 10%. In other embodiments, the activity or expression of forkhead box O1A in an animal is inhibited or decreased by about 30%, or by 50% or more. Thus, the oligomeric compounds modulate expression of forkhead box O1A mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of forkhead box O1A may be measured in serum, adipose tissue, liver or any other body fluid, tissue or organ of the animal. In some embodiments, the cells contained within said fluids, tissues or organs being analyzed contain a nucleic acid molecule encoding forkhead box O1A protein and/or the forkhead box O1A protein itself. Exemplary tissues include, but are not limited to, liver, fat, heart, lung, muscle, pancreas, spleen, testes, ovary, and small intestine.

The compounds of the invention can be utilized in compositions or pharmaceutical compositions by adding an effective amount of a compound to a suitable pharmaceutically acceptable diluent or carrier. Use of the compounds and methods of the invention may also be useful prophylactically.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. Linear compounds, however, are generally more often used. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of antisense compounds useful in this invention include, but are not limited to, oligonucleotides containing modified internucleoside linkages (backbones) such as modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Modified oligonucleotide backbones containing a phosphorus atom therein include, for example, phosphorothioates, chiral-phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage (i.e., a single inverted nucleoside residue which may be abasic—the nucleobase is missing or has a hydroxyl group in place thereof). Various salts, mixed salts and free acid forms may also be included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899;

5,721,218; 5,672,697 and 5,625,050, each of which is herein incorporated by reference in its entirtey.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include, but are not limited to, those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is incorporated herein by reference in its entirety.

In other oligonucleotide mimetics, both the sugar and the internucleoside linkage (i.e., the backbone) of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497-1500.

The compounds of the invention can include phosphorothioate backbones and heteroatom backbones, such as, for example, —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also included are oligonucleotides having morpholino backbone structures of the above-referenced U.S. Pat. No. 5,034,506.

Modified oligonucleotides may also contain one or more substituted sugar moieties. In such cases, oligonucleotides may comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Additional modifications include, but are not limited to, O[$(CH_2)_nO]_mCH_3$, $O(CH_2)_nOCH_3$, $O(CH_2)_nNH_2$, $O(CH_2)_n$ $CH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoallcylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O—(2-methoxyethyl) or 2'-MOE) (Martin et al., Helv. Chim. Acta, 1995, 78, 486-504) (i.e., an alkoxyalkoxy group). Another modification includes 2'-dimethylaminooxyethoxy (i.e., a $O(CH_2)_2ON(CH_3)_2$ group, also known as 2'-DMAOE as described in examples hereinbelow), and 2'-dimethylamino-ethoxyethoxy (also known in the art as 2'-O-dimethyl-amino-ethoxy-ethyl or 2'-DMAEOE, i.e., 2'-O—$CH_2$—O—$CH_2$—N($CH_3$)$_2$, also described in examples hereinbelow).

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is incorporated herein by reference in its entirety.

Another modification of the sugar includes Locked Nucleic Acids (LNAs) in which the 2'-hydroxyl group is linked to the 3' or 4' carbon atom of the sugar ring, thereby forming a bicyclic sugar moiety. The linkage can be a methylene (—$CH_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Additional modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are suitable base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, each of which is incorporated herein by reference.

Another modification of the oligonucleotides of the invention involves chemically linking to the oligonucleotide one or more moieties or conjugates Which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include, but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is incorporated herein by reference in its entirety.

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is incorporated herein by reference in its entirety.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is incorporated herein by reference in its entirety.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention can be prepared as SATE ((S-acetyl-2-thioethyl) phosphate) derivatives according to the methods disclosed in WO 93/24510, WO 94/26764, and U.S. Pat. No. 5,770,713.

The term "pharmaceutically acceptable salts" refers to physiologically and pharmaceutically acceptable salts of the compounds of the invention (i.e., salts that retain the desired biological activity of the parent compound and do not impart undesired toxicological effects thereto). For oligonucleotides, examples of pharmaceutically acceptable salts and their uses are further described in, for example, U.S. Pat. No. 6,287,860, which is incorporated herein by reference in its entirety.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Examples of acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligomeric compounds of the present invention can be utilized for diagnostics, therapeutics, prophylaxis and as research reagents and kits. For therapeutics, an animal, such as a human, suspected of having a disease or disorder which can be treated by modulating the expression of forkhead box O1A is treated by administering oligomeric compounds in accordance with this invention. The compounds of the invention can be utilized in pharmaceutical compositions by adding an effective amount of an oligomeric compound to a suitable pharmaceutically acceptable diluent or carrier. Use of the oligomeric compounds and methods of the invention may also be useful prophylactically, e.g., to prevent or delay infection, inflammation or tumor formation, for example.

The oligomeric compounds of the invention are useful for, inter alia, research and diagnostics, because these compounds hybridize to nucleic acids encoding forkhead box O1A, enabling sandwich and other assays to easily be constructed to exploit this fact. Hybridization of the oligonucleotides of the invention with a nucleic acid encoding forkhead box O1A can be detected by means known in the art. Such means may include, but are not limited to, conjugation of an enzyme to the oligonucleotide, radiolabelling of the oligonucleotide or any other suitable detection means. Kits using such detection means for detecting the level of forkhead box O1A in a sample may also be prepared.

The present invention also includes compositions, pharmaceutical compositions and formulations that include the oligomeric compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular administration. Oligonucleotides with at least one 2'-O-methoxyethyl modification are believed to be particularly useful for oral administration.

Compositions, pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Topical formulations include those in which the oligonucleotides of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Fatty acids and esters include, but are not limited to, arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligonucleotides of the invention are administered in conjunction with one or more penetration enhancers surfactants and chelators. Surfactants include fatty acids and/or esters or salts thereof, bile acids and/or salts thereof. Bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofiisidate. Fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Combinations of penetration enhancers include, for example, fatty acids/salts in combination with bile acids/salts. One combination is the sodium salt of lauric acid, capric acid and UDCA. Additional penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically-heterogenous systems of one liquid dispersed in another in the form of droplets usually exceeding 0.1 μm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug that may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765). Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Ilium et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.). Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates that are attractive candidates for drug delivery vehicles. Transfersomes may be described as lipid droplets that are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, NY, 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylaza-cyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharn. Pharmacol., 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.). Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

EXAMPLES

Example 1

Nucleoside Phosphoramidites for Oligonucleotide Synthesis

Deoxy and 2'-Alkoxy Amidites

2'-Deoxy and 2'-methoxy beta-cyanoethyldiisopropyl phosphor-amidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, optimized synthesis cycles were developed that incorporate multiple steps coupling longer wait times relative to standard synthesis cycles. The following abbreviations are used in the text: thin layer chromatography (TLC), melting point (MP), high pressure liquid chromatography (HPLC), Nuclear Magnetic Resonance (NMR), argon (Ar), methanol (MeOH), dichloromethane ($CH_2Cl_2$), triethylamine (TEA), dimethyl formamide (DMF), ethyl acetate (EtOAc), dimethyl sulfoxide (DMSO), tetrahydrofuran (THF).

Oligonucleotides containing 5-methyl-2'-deoxycytidine (5-Me-dC) nucleotides were synthesized according to published methods (Sanghvi, et. al., Nucleic Acids Research, 1993, 21, 3197-3203) using commercially available phosphoramidites (Glen Research, Sterling Va. or ChemGenes, Needham Mass.) or prepared as follows:

Preparation of 5'-O-Dimethoxytrityl-thymidine intermediate for 5-methyl dC amidite To a 50 L glass reactor equipped with air stirrer and Ar gas line was added thymidine (1.00 kg, 4.13 mol) in anhydrous pyridine (6 L) at ambient temperature. Dimethoxytrityl (DMT) chloride (1.47 kg, 4.34 mol, 1.05 eq) was added as a solid in four portions over 1 h. After 30 min, TLC indicated approx. 95% product, 2% thymidine, 5% DMT reagent and by-products and 2% 3',5'-bis DMT product (Rf in EtOAc 0.45, 0.05, 0.98, 0.95 respectively). Saturated sodium bicarbonate (4 L) and $CH_2Cl_2$ were added with stirring (pH of the aqueous layer 7.5). An additional 18 L of water was added, the mixture was stirred, the phases were separated, and the organic layer was transferred to a second 50 L vessel. The aqueous layer was extracted with additional $CH_2Cl_2$ (2×2 L). The combined organic layer was washed with water (10 L) and then concentrated in a rotary evaporator to approx. 3.6 kg total weight. This was redissolved in $CH_2Cl_2$ (3.5 L), added to the reactor followed by water (6 L) and hexanes (13 L). The mixture was vigorously stirred and seeded to give a fine white suspended solid starting at the interface. After stirring for 1 h, the suspension was removed by suction through a ½" diameter teflon tube into a 20 L suction flask, poured onto a 25 cm Coors Buchner funnel, washed with water (2×3 L) and a mixture of hexanes-$CH_2Cl_2$ (4:1, 2×3 L) and allowed to air dry overnight in pans (1" deep). This was further dried in a vacuum oven (75° C., 0.1 mm Hg, 48 h) to a constant weight of 2072 g (93%) of a white solid, (mp 122-124° C.). TLC indicated a trace contamination of the bis DMT product. NMR spectroscopy also indicated that 1-2 mole percent pyridine and about 5 mole percent of hexanes was still present.

Preparation of 5'-O-Dimethoxytrityl-2'-deoxy-5-methylcytidine intermediate for 5-methyl-dC amidite To a 50 L Schott glass-lined steel reactor equipped with an electric stirrer, reagent addition pump (connected to an addition funnel), heating/cooling system, internal thermometer and an Ar gas line was added 5'-O-dimethoxytrityl-thymidine (3.00 kg, 5.51 mol), anhydrous acetonitrile (25 L) and TEA (12.3 L, 88.4 mol, 16 eq). The mixture was chilled with stirring to −10° C. internal temperature (external −20° C.). Trimethylsilylchloride (2.1 L, 16.5 mol, 3.0 eq) was added over 30 minutes while maintaining the internal temperature below −5° C., followed by a wash of anhydrous acetonitrile (1 L). Note: the reaction is mildly exothermic and copious hydrochloric acid fumes form over the course of the addition. The reaction was allowed to warm to 0° C. and the reaction progress was confirmed by TLC (EtOAc-hexanes 4:1; Rf 0.43 to 0.84 of starting material and silyl product, respectively). Upon completion, triazole (3.05 kg, 44 mol, 8.0 eq) was added the reaction was cooled to −20° C. internal temperature (external −30° C.). Phosphorous oxychloride (1035 mL, 11.1 mol, 2.01 eq) was added over 60 min so as to maintain the temperature between −20° C. and −10° C. during the strongly exothermic process, followed by a wash of anhydrous acetonitrile (1 L). The reaction was warmed to 0° C. and stirred for 1 h. TLC indicated a complete conversion to the triazole product (Rf 0.83 to 0.34 with the product spot glowing in long wavelength UV light). The reaction mixture was a peach-colored thick suspension, which turned darker red upon warming without apparent decomposition. The reaction was cooled to −15° C. internal temperature and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The combined water layers were back-extracted with EtOAc (6 L). The water layer was discarded and the organic layers were concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The second half of the reaction was treated in the same way. Each residue was dissolved in dioxane (3 L) and concentrated ammonium hydroxide (750 mL) was added. A homogenous solution formed in a few minutes and the reaction was allowed to stand overnight (although the reaction is complete within 1 h).

TLC indicated a complete reaction (product Rf 0.35 in EtOAc-MeOH 4:1). The reaction solution was concentrated on a rotary evaporator to a dense foam. Each foam was slowly redissolved in warm EtOAc (4 L; 50° C.), combined in a 50 L glass reactor vessel, and extracted with water (2×4 L) to remove the triazole by-product. The water was back-extracted with EtOAc (2 L). The organic layers were combined and concentrated to about 8 kg total weight, cooled to 0° C. and seeded with crystalline product. After 24 hours, the first crop was collected on a 25 cm Coors Buchner funnel and washed repeatedly with EtOAc (3×3 L) until a white powder was left and then washed with ethyl ether (2×3 L). The solid was put in pans (1" deep) and allowed to air dry overnight. The filtrate was concentrated to an oil, then redissolved in EtOAc (2 L), cooled and seeded as before. The second crop was collected and washed as before (with proportional solvents) and the filtrate was first extracted with water (2×1 L) and then concentrated to an oil. The residue was dissolved in EtOAc (1 L) and yielded a third crop which was treated as above except that more washing was required to remove a yellow oily layer.

After air-drying, the three crops were dried in a vacuum oven (50° C., 0.1 mm Hg, 24 h) to a constant weight (1750, 600 and 200 g, respectively) and combined to afford 2550 g (85%) of a white crystalline product (MP 215-217° C.) when TLC and NMR spectroscopy indicated purity. The mother liquor still contained mostly product (as determined by TLC) and a small amount of triazole (as determined by NMR spectroscopy), bis DMT product and unidentified minor impurities. If desired, the mother liquor can be purified by silica gel chromatography using a gradient of MeOH (0-25%) in EtOAc to further increase the yield.

Preparation of 5'-O-Dimethoxytrityl-2'-deoxy-N4-benzoyl-5-methylcytidine penultimate intermediate for 5-methyl dC amidite Crystalline 5'-O-dimethoxytrityl-5-methyl-2'-deoxycytidine (2000 g, 3.68 mol) was dissolved in anhydrous DMF (6.0 kg) at ambient temperature in a 50 L glass reactor vessel equipped with an air stirrer and argon line. Benzoic anhydride (Chem Impex not Aldrich, 874 g, 3.86 mol, 1.05 eq) was added and the reaction was stirred at ambient temperature for 8 h. TLC ($CH_2Cl_2$-EtOAc; $CH_2Cl_2$-EtOAc 4:1; Rf 0.25) indicated approx. 92% complete reaction. An additional amount of benzoic anhydride (44 g, 0.19 mol) was added. After a total of 18 h, TLC indicated approx. 96% reaction completion. The solution was diluted with EtOAc (20 L), TEA (1020 mL, 7.36 mol, ca 2.0 eq) was added with stirring, and the mixture was extracted with water (15 L, then 2×10 L). The aqueous layer was removed (no back-extraction was needed) and the organic layer was concentrated in 2×20 L rotary evaporator flasks until a foam began to form. The residues were coevaporated with acetonitrile (1.5 L each) and dried (0.1 mm Hg, 25° C., 24 h) to 2520 g of a dense foam. High pressure liquid chromatography (HPLC) revealed a contamination of 6.3% of N4, 3'-O-dibenzoyl product, but very little other impurities.

The product was purified by Biotage column chromatography (5 kg Biotage) prepared with 65:35:1 hexanes-EtOAc-TEA (4 L). The crude product (800 g), dissolved in $CH_2Cl_2$ (2 L), was applied to the column. The column was washed with the 65:35:1 solvent mixture (20 kg), then 20:80:1 solvent mixture (10 kg), then 99:1 EtOAc:TEA (17 kg). The fractions containing the product were collected, and any fractions containing the product and impurities were retained to be resubjected to column chromatography. The column was re-equilibrated with the original 65:35:1 solvent mixture (17 kg). A second batch of crude product (840 g) was applied to the column as before. The column was washed with the following solvent gradients: 65:35:1 (9 kg), 55:45:1 (20 kg), 20:80:1 (10 kg), and 99:1 EtOAc:TEA (15 kg). The column was reequilibrated as above, and a third batch of the crude product (850 g) plus impure fractions recycled from the two previous columns (28 g) was purified following the procedure for the second batch. The fractions containing pure product combined and concentrated on a 20 L rotary evaporator, co-evaporated with acetontirile (3 L) and dried (0.1 mm Hg, 48 h, 25° C.) to a constant weight of 2023 g (85%) of white foam and 20 g of slightly contaminated product from the third run. HPLC indicated a purity of 99.8% with the balance as the diBenzoyl product.

[5'-O-(4,4'-Dimethoxytriphenylmethyl)-2'-deoxy-N4-benzoyl-5-methylcytidin-3'-O-yl]-2-cyanoethyl-N,N-diisopropylphosphoramidite (5-methyl dC amidite)

5'-O-(4,4'-Dimethoxytriphenylmethyl)-2'-deoxy-N4-benzoyl-5-methylcytidine (998 g, 1.5 mol) was dissolved in anhydrous DMF (2 L). The solution was co-evaporated with toluene (300 ml) at 50° C. under reduced pressure, then cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (15 ml) was added and the mixture was left at room temperature for 5 hours. TEA (300 ml) was added, the mixture was diluted with DMF (2.5 L) and water (600 ml), and extracted with hexane (3×3 L). The mixture was diluted with water (1.2 L) and extracted with a mixture of toluene (7.5 L) and hexane (6 L). The two layers were separated, the upper layer was washed with DMF-water (7:3 v/v, 3×2 L) and water (3×2 L), and the phases were separated. The organic layer was dried ($Na_2SO_4$), filtered and rotary evaporated. The residue was co-evaporated with acetonitrile (2×2 L) under reduced pressure and dried to a constant weight (25° C., 0.1 mm Hg, 40 h) to afford 1250 g an off-white foam solid (96%).

2'-Fluoro amidites

2'-Fluorodeoxyadenosine amidites

2'-fluoro oligonucleotides were synthesized as described previously (Kawasaki, et. al., J. Med. Chem., 1993, 36, 831-841) and U.S. Pat. No. 5,670,633, herein incorporated by reference. The preparation of 2'-fluoropyrimidines containing a 5-methyl substitution are described in U.S. Pat. No. 5,861,493. Briefly, the protected nucleoside N6-benzoyl-2'-deoxy-2'-fluoroadenosine was synthesized utilizing commercially available 9-beta-D-arabinofuranosyl-adenine as starting material and whereby the 2'-alpha-fluoro atom is introduced by a SN2-displacement of a 2'-beta-triflate group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate isobutyryl-arabinofuranosylguanosine. Alternatively, isobutyryl-arabinofuranosylguanosine was prepared as described by Ross et al., (Nucleosides & Nucleosides, 16, 1645, 1997). Deprotection of the TPDS group was followed by protection of the hydroxyl group with THP to give isobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'-phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites (otherwise known as MOE amidites) are prepared as follows, or alternatively, as per the methods of Martin, P., (Helvetica Chimica Acta, 1995, 78, 486-504).

Preparation of 2'-O-(2-methoxyethyl)-5-methyluridine intermediate 2,2'-Anhydro-5-methyl-uridine (2000 g, 8.32 mol), tris(2-methoxyethyl)borate (2504 g, 10.60 mol), sodium bicarbonate (60 g, 0.70 mol) and anhydrous 2-methoxyethanol (5 L) were combined in a 12 L three necked flask and heated to 130° C. (internal temp) at atmospheric pressure, under an argon atmosphere with stirring for 21 h. TLC indicated a complete reaction. The solvent was removed under reduced pressure until a sticky gum formed (50-85° C. bath temp and 100-11 mm Hg) and the residue was redissolved in water (3 L) and heated to boiling for 30 min in order the hydrolyze the borate esters. The water was removed under reduced pressure until a foam began to form and then the process was repeated. HPLC indicated about 77% product, 15% dimer (5' of product attached to 2' of starting material) and unknown derivatives, and the balance was a single unresolved early eluting peak.

The gum was redissolved in brine (3 L), and the flask was rinsed with additional brine (3 L). The combined aqueous solutions were extracted with chloroform (20 L) in a heavier-than continuous extractor for 70 h. The chloroform layer was concentrated by rotary evaporation in a 20 L flask to a sticky foam (2400 g). This was coevaporated with MeOH (400 mL) and EtOAc (8 L) at 75° C. and 0.65 atm until the foam dissolved at which point the vacuum was lowered to about 0.5 atm. After 2.5 L of distillate was collected a precipitate began to form and the flask was removed from the rotary evaporator and stirred until the suspension reached ambient temperature. EtOAc (2 L) was added and the slurry was filtered on a 25 cm table top Buchner funnel and the product was washed with EtOAc (3×2 L). The bright white solid was air dried in pans for 24 h then further dried in a vacuum oven (50° C., 0.1 mm Hg, 24 h) to afford 1649 g of a white crystalline solid (mp 115.5-116.5° C.).

The brine layer in the 20 L continuous extractor was further extracted for 72 h with recycled chloroform. The chloroform was concentrated to 120 g of oil and this was combined with the mother liquor from the above filtration (225 g), dissolved in brine (250 mL) and extracted once with chloroform (250 mL). The brine solution was continuously extracted and the product was crystallized as described above to afford an additional 178 g of crystalline product containing about 2% of thymine. The combined yield was 1827 g (69.4%). HPLC indicated about 99.5% purity with the balance being the dimer.

Preparation of 5'-O-DMT-2'-O-(2-methoxyethyl)-5-methyluridine penultimate intermediate In a 50 L glass-lined steel reactor, 2'-O-(2-methoxyethyl)-5-methyl-uridine (MOE-T, 1500 g, 4.738 mol), lutidine (1015 g, 9.476 mol) were dissolved in anhydrous acetonitrile (15 L). The solution was stirred rapidly and chilled to −10° C. (internal temperature). Dimethoxytriphenylmethyl chloride (1765.7 g, 5.21 mol) was added as a solid in one portion. The reaction was allowed to warm to −2° C. over 1 h. (Note: The reaction was monitored closely by TLC (EtOAc) to determine when to stop the reaction so as to not generate the undesired bis-DMT substituted side product). The reaction was allowed to warm from −2 to 3° C. over 25 min. then quenched by adding MeOH (300 mL) followed after 10 min by toluene (16 L) and water (16 L). The solution was transferred to a clear 50 L vessel with a bottom outlet, vigorously stirred for 1 minute, and the layers separated. The aqueous layer was removed and the organic layer was washed successively with 10% aqueous citric acid (8 L) and water (12 L). The product was then extracted into the aqueous phase by washing the toluene solution with aqueous sodium hydroxide (0.5N, 16 L and 8 L). The combined aqueous layer was overlayed with toluene (12 L) and solid citric acid (8 moles, 1270 g) was added with vigorous stirring to lower the pH of the aqueous layer to 5.5 and extract the product into the toluene. The organic layer was washed with water (10 L) and TLC of the organic layer indicated a trace of DMT-O-Me, bis DMT and dimer DMT.

The toluene solution was applied to a silica gel column (6 L sintered glass funnel containing approx. 2 kg of silica gel slurried with toluene (2 L) and TEA (25 mL)) and the fractions were eluted with toluene (12 L) and EtOAc (3×4 L) using vacuum applied to a filter flask placed below the column. The first EtOAc fraction containing both the desired product and impurities were resubjected to column chromatography as above. The clean fractions were combined, rotary evaporated to a foam, coevaporated with acetonitrile (6 L) and dried in a vacuum oven (0.1 mm Hg, 40 h, 40° C.) to afford 2850 g of a white crisp foam. NMR spectroscopy indicated a 0.25 mole % remainder of acetonitrile (calculates to be approx. 47 g) to give a true dry weight of 2803 g (96%). HPLC indicated that the product was 99.41% pure, with the remainder being 0.06 DMT-O-Me, 0.10 unknown, 0.44 bis DMT, and no detectable dimer DMT or 3'-O-DMT.

Preparation of [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite)

5'-O-(4,4'-Dimethoxytriphenylmethyl)-2'-O-(2-methoxyethyl)-5-methyluridine (1237 g, 2.0 mol) was dissolved in anhydrous DMF (2.5 L). The solution was co-evaporated with toluene (200 ml) at 50° C. under reduced pressure, then cooled to room temperature and 2-cyanoethyl tetraisopropylphosphorodiamidite (900 g, 3.0 mol) and tetrazole (70 g, 1.0 mol) were added. The mixture was shaken until all tetrazole was dissolved, N-methylimidazole (20 ml) was added and the solution was left at room temperature for 5 hours. TEA (300 ml) was added, the mixture was diluted with DMF (3.5 L) and water (600 ml) and extracted with hexane (3×3 L). The mixture was diluted with water (1.6 L) and extracted with the mixture of toluene (12 L) and hexanes (9 L). The upper layer was washed with DMF-water (7:3 v/v, 3×3 L) and water (3×3 L). The organic layer was dried (Na2SO4), filtered and evaporated. The residue was co-evaporated with acetonitrile (2×2 L) under reduced pressure and dried in a vacuum oven (25° C., 0.1 mm Hg, 40 h) to afford 1526 g of an off-white foamy solid (95%).

Preparation of 5'-O-Dimethoxytrityl-2'-O-(2-methoxyethyl)-5-methylcytidine intermediate To a 50 L Schott glass-lined steel reactor equipped with an electric stirrer, reagent addition pump (connected to an addition funnel), heating/cooling system, internal thermometer and argon gas line was added 5'-O-dimethoxytrityl-2'-O-(2-methoxyethyl)-5-methyl-uridine (2.616 kg, 4.23 mol, purified by base extraction only and no scrub column), anhydrous acetonitrile (20 L), and TEA (9.5 L, 67.7 mol, 16 eq). The mixture was chilled with stirring to −10° C. internal temperature (external −20° C.). Trimethylsilylchloride (1.60 L, 12.7 mol, 3.0 eq) was added over 30 min. while maintaining the internal temperature below −5° C., followed by a wash of anhydrous acetonitrile (1 L). (Note: the reaction is mildly exothermic and copious hydrochloric acid fumes form over the course of the addition). The reaction was allowed to warm to 0° C. and the reaction progress was confirmed by TLC (EtOAc, Rf 0.68 and 0.87 for starting material and silyl product, respectively). Upon completion, triazole (2.34 kg, 33.8 mol, 8.0 eq) was added the reaction was cooled to −20° C. internal temperature (external −30° C.). Phosphorous oxychloride (793 mL, 8.51 mol, 2.01 eq) was added slowly over 60 min so as to maintain the temperature between −20° C. and −10° C. (note: strongly exothermic), followed by a wash of anhydrous acetonitrile (1 L). The reaction was warmed to 0° C. and stirred for 1 h, at which point it was an off-white thick suspension. TLC indicated a complete conversion to the triazole product (EtOAc, Rf 0.87 to 0.75 with the product spot glowing in long wavelength UV light). The reaction was cooled to −15° C. and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The second half of the reaction was treated in the same way. The combined aqueous layers were back-extracted with EtOAc (8 L) The organic layers were combined and concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The residue was dissolved in dioxane (2 L) and concentrated ammonium hydroxide (750 mL) was added. A homogenous solution formed in a few minutes and the reaction was allowed to stand overnight TLC indicated a complete reaction (CH2Cl2-acetone-MeOH, 20:5:3, Rf 0.51). The reaction solution was concentrated on a rotary evaporator to a dense foam and slowly redissolved in warm $CH_2Cl_2$ (4 L, 40° C.) and transferred to a 20 L glass extraction vessel equipped with a air-powered stirrer. The organic layer was extracted with water (2×6 L) to remove the triazole by-product. (Note: In the first extraction an emulsion formed which took about 2 h to resolve). The water layer was back-extracted with $CH_2Cl_2$ (2×2 L), which in turn was washed with water (3 L). The combined organic layer was concentrated in 2×20 L flasks to a gum and then recrystallized from EtOAc seeded with crystalline product. After sitting overnight, the first crop was collected on a 25 cm Coors Buchner funnel and washed repeatedly with EtOAc until a white free-flowing powder was left (about 3×3 L). The filtrate was concentrated to an oil recrystallized from EtOAc, and collected as above. The solid was air-dried in pans for 48 h, then further dried in a vacuum oven (50° C., 0.1 mm Hg, 17 h) to afford 2248 g of a bright white, dense solid (86%). An HPLC analysis indicated both crops to be 99.4% pure and NMR spectroscopy indicated only a faint trace of EtOAc remained.

Preparation of 5'-O-dimethoxytrityl-2'-O-(2-methoxyethyl)-N4-benzoyl-5-methyl-cytidine penultimate intermediate Crystalline 5'-O-dimethoxytrityl-2'-O-(2-methoxyethyl)-5-methyl-cytidine (1000 g, 1.62 mol) was suspended in anhydrous DMF (3 kg) at ambient temperature and stirred under an Ar atmosphere. Benzoic anhydride (439.3 g, 1.94 mol) was added in one portion. The solution clarified after 5 hours and was stirred for 16 h. HPLC indicated 0.45% starting material remained (as well as 0.32% N4, 3'-O-bis Benzoyl). An additional amount of benzoic anhydride (6.0 g, 0.0265 mol) was added and after 17 h, HPLC indicated no starting material was present. TEA (450 mL, 3.24 mol) and toluene (6 L) were added with stirring for 1 minute. The solution was washed with water (4×4 L), and brine (2×4 L). The organic layer was partially evaporated on a 20 L rotary evaporator to remove 4 L of toluene and traces of water. HPLC indicated that the bis benzoyl side product was present as a 6% impurity. The residue was diluted with toluene (7 L) and anhydrous DMSO (200 mL, 2.82 mol) and sodium hydride (60% in oil, 70 g, 1.75 mol) was added in one portion with stirring at ambient temperature over 1 h. The reaction was quenched by slowly adding then washing with aqueous citric acid (10%, 100 mL over 10 min, then 2×4 L), followed by aqueous sodium bicarbonate (2%, 2 L), water (2×4 L) and brine (4 L). The organic layer was concentrated on a 20 L rotary evaporator to about 2 L total volume. The residue was purified by silica gel column chromatography (6 L Buchner funnel containing 1.5 kg of silica gel wetted with a solution of EtOAc-hexanes-TEA (70:29:1)). The product was eluted with the same solvent (30 L) followed by straight EtOAc (6 L). The fractions containing the product were combined, concentrated on a rotary evaporator to a foam and then dried in a vacuum oven (50° C., 0.2 mm Hg, 8 h) to afford 1155 g of a crisp, white foam (98%). HPLC indicated a purity of >99.7%.

Preparation of [5'-O-(4,4'-Dimethoxytriphenylmethyl)-2'-O-(2-methoxyethyl)-N4-benzoyl-5-methylcytidin-3'-O-yl]-2-cyanoethyl-N,N-diisopropylphosphoramidite (MOE 5-Me-C amidite)

5'-O-(4,4'-Dimethoxytriphenylmethyl)-2'-O-(2-methoxyethyl)-N4-benzoyl-5-methylcytidine (1082 g, 1.5 mol) was dissolved in anhydrous DMF (2 L) and co-evaporated with toluene (300 ml) at 50° C. under reduced pressure. The mixture was cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (30 ml) was added, and the mixture was left at room temperature for 5 hours. TEA (300 ml) was added, the mixture was diluted with DMF (1 L) and water (400 ml) and extracted with hexane (3×3 L). The mixture was diluted with water (1.2 L) and extracted with a mixture of toluene (9 L) and hexanes (6 L). The two layers were separated and the upper layer was washed with DMF-water (60:40 v/v, 3×3 L) and water (3×2 L). The organic layer was dried (Na2SO4), filtered and evaporated. The residue was co-evaporated with acetonitrile (2×2 L) under reduced pressure and dried in a vacuum oven (25° C., 0.1 mm Hg, 40 h) to afford 1336 g of an off-white foam (97%).

Preparation of [5'-O-(4,4'-Dimethoxytriphenylmethyl)-2'-O-(2-methoxyethyl)-N6-benzoyladenosin-3'-O-yl]-2-cyanoethyl-N,N-diisopropylphosphoramidite (MOE A amdite)

5'-O-(4,4'-Dimethoxytriphenylmethyl)-2'-O-(2-methoxyethyl)-N6-benzoyladenosine (purchased from Reliable Biopharmaceutical, St. Lois, Mo.), 1098 g, 1.5 mol) was dissolved in anhydrous DMF (3 L) and co-evaporated with toluene (300 ml) at 50° C. The mixture was cooled to room temperature and 2-cyanoethyl tetraisopropylphosphorodiamidite (680 g, 2.26 mol) and tetrazole (78.8 g, 1.24 mol) were added. The mixture was shaken until all tetrazole was dissolved, N-methylimidazole (30 ml) was added, and mixture was left at room temperature for 5 hours. TEA (300 ml) was added, the mixture was diluted with DMF (1 L) and water (400 ml) and extracted with hexanes (3×3 L). The mixture was diluted with water (1.4 L) and extracted with the mixture of toluene (9 L) and hexanes (6 L). The two layers were separated and the upper layer was washed with DMF-water (60:40, v/v, 3×3 L) and water (3×2 L). The organic layer was dried ($Na_2SO_4$), filtered and evaporated to a sticky foam. The residue was co-evaporated with acetonitrile (2.5 L) under reduced pressure and dried in a vacuum oven (25° C., 0.1 mm Hg, 40 h) to afford 1350 g of an off-white foam solid (96%).

Prepartion of [5'-O-(4,4'-Dimethoxytriphenylmethyl)-2'-O-(2-methoxyethyl)-N4-isobuonylguanosin-3'-O-yl]-2-cyanoethyl-N,N-diisopropylphosphoramidite (MOE G amidite)

5'-O-(4,4'-Dimethoxytriphenylmethyl)-2'-O-(2-methoxyethyl)-N4-isobutyrlguanosine (purchased from Reliable Biopharmaceutical, St. Louis, Mo., 1426 g, 2.0 mol) was dissolved in anhydrous DMF (2 L). The solution was co-evaporated with toluene (200 ml) at 50° C., cooled to room temperature and 2-cyanoethyl tetraisopropylphosphorodiamidite (900 g, 3.0 mol) and tetrazole (68 g, 0.97 mol) were added. The mixture was shaken until all tetrazole was dissolved, N-methylimidazole (30 ml) was added, and the mixture was left at room temperature for 5 hours. TEA (300 ml) was added, the mixture was diluted with DMF (2 L) and water (600 ml) and extracted with hexanes (3×3 L). The mixture was diluted with water (2 L) and extracted with a mixture of toluene (10 L) and hexanes (5 L). The two layers were separated and the upper layer was washed with DMF-water (60:40, v/v, 3×3 L). EtOAc (4 L) was added and the solution was washed with water (3×4 L). The organic layer was dried ($Na_2SO_4$), filtered and evaporated to approx. 4 kg. Hexane (4 L) was added, the mixture was shaken for 10 min, and the supernatant liquid was decanted. The residue was co-evaporated with acetonitrile (2×2 L) under reduced pressure and dried in a vacuum oven (25° C., 0.1 mm Hg, 40 h) to afford 1660 g of an off-white foamy solid (91%).

2'-O-(Aminooxyethyl)nucleoside amidites and 2'-O-(dimethylamino-oxy-ethyl)nucleoside amidites 2'-(Dimethylaminooxyethoxy)nucleoside amidites 2'-(Dimethylaminooxyethoxy)nucleoside amidites (also known in the art as 2'-O-(dimethylaminooxyethyl)nucleoside amidites) are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O2-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, EtOAc) indicated a complete reaction. The solution was concentrated under reduced pressure to a thick oil. This was partitioned between $CH_2Cl_2$ (1 L) and saturated sodium bicarbonate (2×1 L) and brine (1 L). The organic layer was dried over sodium sulfate, filtered, and concentrated under reduced pressure to a thick oil. The oil was dissolved in a 1:1 mixture of EtOAc and ethyl ether (600 mL) and cooling the solution to −10° C. afforded a white crystalline solid which was collected by filtration, washed with ethyl ether (3×200 mL) and dried (40° C., 1 mm Hg, 24 h) to afford 149 g of white solid (74.8%). TLC and NMR spectroscopy were consistent with pure product.

5-O-tert-Butyldiphenylsilyl-2'-O-(2-hydroxyethyl)-5-methyluridine

In the fume hood, ethylene glycol (350 mL, excess) was added cautiously with manual stirring to a 2 L stainless steel pressure reactor containing borane in tetrahydrofuran (1.0 M, 2.0 eq, 622 mL). (Caution: evolves hydrogen gas). 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient temperature and opened. mc (EtOAc, Rf 0.67 for desired product and Rf 0.82 for ara-T side product) indicated about 70% conversion to the product. The solution was concentrated under reduced pressure (10 to 1 mm Hg) in a warm water bath (40-100° C.) with the more extreme conditions used to remove the ethylene glycol. (Alternatively, once the THF has evaporated the solution can be diluted with water and the product extracted into EtOAc). The residue was purified by column chromatography (2 kg silica gel, EtOAc-hexanes gradient 1:1 to 4:1). The appropriate fractions were combined, evaporated and dried to afford 84 g of a white crisp foam (50%), contaminated starting material (17.4 g, 12% recovery) and pure reusable starting material (20 g, 13% recovery). TLC and NMR spectroscopy were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol) and dried over P2O5 under high vacuum for two days at 40° C. The reaction mixture was flushed with argon and dissolved in dry THF (369.8 mL, Aldrich, sure seal bottle). Diethyl-azodicarboxylate (6.98 mL, 44.36 mmol) was added dropwise to the reaction mixture with the rate of addition maintained such that the resulting deep red coloration is just discharged before adding the next drop. The reaction mixture was stirred for 4 hrs., after which time TLC (EtOAc:hexane, 60:40) indicated that the reaction was complete. The solvent was evaporated in vacuuo and the residue purified by flash column chromatography (eluted with 60:40 EtOAc:hexane), to yield 2'-O-([2-phthalimidoxy)ethyl]-5'-t-butyldiphenylsilyl-5-methyluridine as white foam (21.819 g, 86%) upon rotary evaporation.

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate washed with ice cold $CH_2Cl_2$, and the combined organic phase was washed with water and brine and dried (anhydrous $Na_2SO_4$). The solution was filtered and evaporated to afford 2'-O-(aminooxyethyl)thymidine, which was then dissolved in MeOH (67.5 mL). Formaldehyde (20% aqueous solution, w/w, 1.1 eq.) was added and the resulting mixture was stirred for 1 h. The solvent was removed under vacuum and the residue was purified by column chromatography to yield 5'-O-tert-butyldiphenylsilyl-2'-O-[(2-formadoximinooxy)ethyl]-5-methyluridine as white foam (1.95 g, 78%) upon rotary evaporation.

5'-O-tert-Butyldiphenylsilyl-2'-O-[N,N dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL) and cooled to 10° C. under inert atmosphere. Sodium cyanoborohydride (0.39 g, 6.13 mmol) was added and the reaction mixture was stirred. After 10 minutes the reaction was warmed to room temperature and stirred for 2 h. while the progress of the reaction was monitored by TLC (5% MeOH in $CH_2Cl_2$). Aqueous $NaHCO_3$ solution (5%, 10 mL) was added and the product was extracted with EtOAc (2×20 mL). The organic phase was dried over anhydrous $Na_2SO_4$, filtered, and evaporated to dryness. This entire procedure was repeated with the resulting residue, with the exception that formaldehyde (20% w/w, 30 mL, 3.37 mol) was added upon dissolution of the residue in the PPTS/MeOH solution. After the extraction and evaporation, the residue was purified by flash column chromatography and (eluted with 5% MeOH in $CH_2Cl_2$) to afford 5'-O-tert-butyldiphenylsilyl-2'-O-[N,N-dimethylaminooxyethyl]-5-methyluridine as a white foam (14.6 g, 80%) upon rotary evaporation.

2'-O-(dimethylaminooxyethyl)-5-methyluridine

Triethylamine trihydrofluoride (3.91 mL, 24.0 mmol) was dissolved in dry THF and TEA (1.67 mL, 12 mmol, dry, stored over KOH) and added to 5'-O-tert-butyldiphenylsilyl-2'-O-[N,N-dimethylaminooxyethyl]-5-methyluridine (1.40 g, 2.4 mmol). The reaction was stirred at room temperature for 24 hrs and monitored by TLC (5% MeOH in $CH_2Cl_2$). The solvent was removed under vacuum and the residue purified by flash column chromatography (eluted with 10% MeOH in $CH_2Cl_2$) to afford 2'-O-(dimethylaminooxyethyl)-5-methyluridine (766 mg, 92.5%) upon rotary evaporation of the solvent.

5-O-DMT-2'-O-(dimethylaminocayethyl)-5-methyluridine

2'-O-(dimethylaminooxyethyl)-5-methyluridine (750 mg, 2.17 mmol) was dried over P2O5 under high vacuum overnight at 40° C., co-evaporated with anhydrous pyridine (20 mL), and dissolved in pyridine (11 mL) under argon atmosphere. 4-dimethylaminopyridine (26.5 mg, 2.60 mmol) and 4,4'-dimethoxytrityl chloride (880 mg, 2.60 mmol) were added to the pyridine solution and the reaction mixture was stirred at room temperature until all of the starting material had reacted. Pyridine was removed under vacuum and the residue was purified by column chromatography (eluted with 10% MeOH in $CH_2Cl_2$ containing a few drops of pyridine) to yield 5'-O-DMT-2'-O-(dimethylamino-oxyethyl)-5-methyluridine (1.13 g, 80%) upon rotary evaporation.

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL), N,N-diisopropylamine tetrazonide (0.29 g, 1.67 mmol) was added and the mixture was dried over $P_2O_5$ under high vacuum overnight at 40° C. This was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 h under inert atmosphere. The progress of the reaction was monitored by TLC (hexane:EtOAc 1:1). The solvent was evaporated, then the residue was dissolved in EtOAc (70 mL) and washed with 5% aqueous $NaHCO_3$ (40 mL). The EtOAc layer was dried over anhydrous $Na_2SO_4$, filtered, and concentrated. The residue obtained was purified by column chromatography (EtOAc as eluent) to afford 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%) upon rotary evaporation.

2'-(Aminooxyethoxy)nucleoside amidites

2'-(Aminooxyethoxy)nucleoside amidites (also known in the art as 2'-O-(aminooxyethyl)nucleoside amidites) are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl)diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may be phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethyl-amino-ethoxy-ethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2"-O-[2(2-N,N-dimethylaminoethoxy)ethyl]-5-methyl uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. (Caution: Hydrogen gas evolves as the solid dissolves). O2-,2'-anhydro-5-methyluridine (1.2 g, 5 mmol), and sodium bicarbonate (2.5 mg) were added and the bomb was sealed, placed in an oil bath and heated to 155° C. for 26 h. then cooled to room temperature. The crude solution was concentrated, the residue was diluted with water (200 mL) and extracted with hexanes (200 mL). The product was extracted from the aqueous layer with EtOAc (3×200 mL) and the combined organic layers were washed once with water, dried over anhydrous sodium sulfate, filtered and concentrated. The residue was purified by silica gel column chromatography (eluted with 5:100:2 MeOH/$CH_2Cl_2$/TEA) as the eluent. The appropriate fractions were combined and evaporated to afford the product as a white solid.

5'-O-dimethoxytrityl-2'-O-[2(2-N,N-dimethyl-aminoethoxy)-ethyl)]-5-methyl uridine To 0.5 g (1.3 mmol) of 2'-O-[2(2-N,N-dimethyl-aminoethoxy)ethyl)]-5-methyl uridine in anhydrous pyridine (8 mL), was added TEA (0.36 mL) and dimethoxytrityl chloride (DMT-Cl, 0.87 g, 2 eq.) and the reaction was stirred for 1 h. The reaction mixture was poured into water (200 mL) and extracted with $CH_2Cl_2$ (2×200 mL). The combined $CH_2Cl_2$ layers were washed with saturated $NaHCO_3$ solution, followed by saturated NaCl solution, dried over anhydrous sodium sulfate, filtered and evaporated. The residue was purified by silica gel column chromatography (eluted with 5:100:1 $MeOH/CH_2Cl_2/TEA$) to afford the product.

5'-O-Dimethoxytrityl-2'-O-[2(2-N,N-dimethylamino-ethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylamino-ethoxy)-ethyl)]-5-methyluridine (2.17 g, 3 mmol) dissolved in $CH_2Cl_2$ (20 mL) under an atmosphere of argon. The reaction mixture was stirred overnight and the solvent evaporated. The resulting residue was purified by silica gel column chromatography with EtOAc as the eluent to afford the title compound.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligo-nucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

PNA Synthesis

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, and 5,719,262, herein incorporated by reference.

Example 4

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphor-amidite for the DNA portion and 5'-dimethoxy-trityl-2'-O-methyl-3'-O-phosphoramidite for 5' and 3' wings. The standard synthesis cycle is modified by incorporating coupling steps with increased reaction times for the 5'-dimethoxy-trityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxyl]-[2'-O-(Methoxyethyl)]Chimeric Phosphorothioate Oligonucleotides

[2'-O-(2-methoxyethyl)]-[2'-deoxy]-[2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy-Phosphoro-thioate]-[2'-O-(2-Methoxyethyl)Phosphodiester]Chimeric Oligo-nucleo-tides

[2'-O-(2-methoxyethyl phosphodiester]-[2'-deoxy phosphorothioate]-[2'-O-(methoxyethyl)phosphodiester]chimeric oligonucleo-tides are prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Design and Screening of Duplexed Compounds Targeting Forkhead Box O1A

In accordance with the present invention, a series of nucleic acid duplexes comprising the antisense compounds of the present invention and their complements can be designed to target forkhead box O1A. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:169) and having a two-nucleobase overhang of deoxythymidine(dT) would have the following structure:

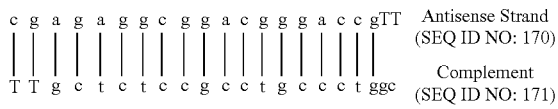

Antisense Strand (SEQ ID NO: 170)
Complement (SEQ ID NO: 171)

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate forkhead box O1A expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 7

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 8

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 9

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 10

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.
T-24 Cells:
The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.
A549 Cells:
The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by typsinization and dilution when they reached 90% confluence.
NHDF Cells:
Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.
HEK Cells:
Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.
b.END Cells:
The mouse brain endothelial cell line b.END was obtained from Dr. Werner Risau at the Max Plank Institutte (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.
Treatment with Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO:1) which is targeted to human H-ras, or ISIS 18078, (GTGCGCGCGAGCCCGAAATC, SEQ ID NO:2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO:3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 11

Analysis of Oligonucleotide Inhibition of Forkhead Box O1A Expression

Antisense modulation of forkhead box O1A expression can be assayed in a variety of ways known in the art. For example, forkhead box O1A mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of forkhead box O1A can be quantitated in a variety of ways well known in the art, such as immunoprecipitation, Western blot analysis (immunoblotting), ELISA or fluorescence-activated cell sorting (FACS). Antibodies directed to forkhead box O1A can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., (Current Protocols in Molecular Biology, Volume 2, pp. 11.12.1-11.12.9, John Wiley & Sons, Inc., 1997). Preparation of monoclonal antibodies is taught in, for example, Ausubel, F. M. et al., (Current Protocols in Molecular Biology, Volume 2, pp. 11.4.1-11.11.5, John Wiley & Sons, Inc., 1997).

Immunoprecipitation methods are standard in the art and can be found at, for example, Ausubel, F. M. et al., (Current Protocols in Molecular Biology, Volume 2, pp. 10.16.1-10.16.11, John Wiley & Sons, Inc., 1998). Western blot (immunoblot) analysis is standard in the art and can be found at, for example, Ausubel, F. M. et al., (Current Protocols in Molecular Biology, Volume 2, pp. 10.8.1-10.8.21, John Wiley & Sons, Inc., 1997). Enzyme-linked immunosorbent assays (ELISA) are standard in the art and can be found at, for example, Ausubel, F. M. et al., (Current Protocols in Molecular Biology, Volume 2, pp. 11.2.1-11.2.22, John Wiley & Sons, Inc., 1991).

Example 12

Design of Phenotypic Assays and in Vivo Studies for the Use of Forkhead Box O1A Inhibitors Phenotypic Assays Once forkhead box O1A inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of forkhead box O1A in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with forkhead box O1A inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the forkhead box O1A inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study. To account for the psychological effects of receiving treatments, volunteers are randomly given placebo or forkhead box O1A inhibitor. Furthermore, to prevent the doctors from being biased in treatments, they are not informed as to whether the medication they are administering is a forkhead box O1A inhibitor or a placebo. Using this randomization approach, each volunteer has the same chance of being given either the new treatment or the placebo.

Volunteers receive either the forkhead box O1A inhibitor or placebo for eight week period with biological parameters associated with the indicated disease state or condition being measured at the beginning (baseline measurements before any treatment), end (after the fmal treatment), and at regular intervals during the study period. Such measurements include the levels of nucleic acid molecules encoding forkhead box O1A or forkhead box O1A protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and forkhead box O1A inhibitor treatment. In general, the volunteers treated with placebo have little or no response to treatment, whereas the volunteers treated with the forkhead box O1A inhibitor show positive trends in their disease state or condition index at the conclusion of the study.

Example 13

Poly(A)+ mRNA Isolation

Poly(A)+ mRNA was isolated according to Miura et al., (Clin. Chem., 1996, 42, 1758-1764). Other methods for poly (A)+ mRNA isolation are taught in, for example, Ausubel, F. M. et al., (Current Protocols in Molecular Biology, Volume 1, pp. 4.5.1-4.5.3, John Wiley & Sons, Inc., 1993). Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70 µC, was added to each well, the plate was incubated on a 90 µC hot plate for 5 minutes, and the eluate was then transferred to a fresh 96-well plate.

Cells grown on 100 mm or other standard plates may be treated similarly, using appropriate volumes of all solutions.

Example 14

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 15

Real-Time Quantitative PCR Analysis of Forkhead Box O1A mRNA Levels

Quantitation of forkhead box O1A mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer (—MgCl2), 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, (Analytical Biochemistry, 1998, 265, 368-374).

In this assay, 170 µl, of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 480 nm and emission at 520 nm.

Probes and primers to human forkhead box O1A were designed to hybridize to a human forkhead box O1A sequence, using published sequence information (GenBank accession number NM_002015.2, incorporated herein as SEQ ID NO:4). For human forkhead box O1A the PCR primers were:

```
forward primer:
GCAATCCCGAAAACATGGAA      (SEQ ID NO: 5)

reverse primer:
CAGGTGAGGACTGGGTCGAA      (SEQ ID NO: 6)
``` and the PCR probe was:

```
                                         (SEQ ID NO: 7)
FAM-TGGATAATCTCAACCTTCTCTCATCACCAACATC-TAMRA
``` where FAM is the fluorescent dye and TAMRA is the quencher dye. For human GAPDH the PCR primers were:

```
forward primer:
GAAGGTGAAGGTCGGAGTC       (SEQ ID NO: 8)

reverse primer:
GAAGATGGTGATGGGATTTC      (SEQ ID NO: 9)
``` and the PCR probe was:

```
                                        (SEQ ID NO: 10)
5' JOE-CAAGCTTCCCGTTCTCAGCC-TAMRA 3'
``` where JOE is the fluorescent reporter dye and TAMRA is the quencher dye.

Probes and primers to mouse forkhead box O1A were designed to hybridize to a mouse forkhead box O1A sequence, using published sequence information (GenBank accession number AJ252157.1, incorporated herein as SEQ ID NO:11). For mouse forkhead box O1A the PCR primers were:

```
forward primer:
CAAAGTACACATACGGCCAATCC   (SEQ ID NO: 12)

reverse primer:
CGTAACTTGATTTGCTGTCCTGAA  (SEQ ID NO: 13)
``` and the PCR probe was:

```
FAM-TGAGCCCTTTGCCCCAGATGCCTAT-TAMRA  (SEQ ID NO: 14)
``` where FAM is the fluorescent reporter dye and TAMRA is the quencher dye. For mouse GAPDH the PCR primers were:

```
forward primer:
GGCAAATTCAACGGCACAGT      (SEQ ID NO: 15)

reverse primer:
GGGTCTCGCTCCTGGAAGAT      (SEQ ID NO: 16)
``` and the PCR probe was:

```
                                        (SEQ ID NO: 17)
5' JOE-AAGGCCGAGAATGGGAAGCTTGTCATC-TAMRA 3'
``` where JOE is the fluorescent reporter dye and TAMRA is the quencher dye.

Example 16

Northern Blot Analysis of Forkhead Box O1A mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human forkhead box O1A, a human forkhead box O1A specific probe was prepared by PCR using the forward primer GCAATCCCGAAAACATGGAA (SEQ ID NO:5) and the reverse primer CAGGTGAGGACTGGGTCGAA (SEQ ID NO:6). To normalize for variations in loading and transfer efficiency membranes were stripped and probed for human glyceraldehyde-3-phosphate dehydrogenase (GAPDH) RNA (Clontech, Palo Alto, Calif.).

To detect mouse forkhead box O1A, a mouse forkhead box O1A specific probe was prepared by PCR using the forward primer CAAAGTACACATACGGCCAATCC (SEQ ID NO:12) and the reverse primer CGTAACTTGATTTGCT-GTCCTGAA (SEQ ID NO:13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 17

Modulation of Human Forkhead Box O1A Expression by Chimeric Phosphorothioate Oligonucleotides Having 2'-MOE Wings and a Deoxy Gap In accordance with the present invention, a series of oligonucleotides were designed to target different regions of the human forkhead box O1A RNA, using published sequences (GenBank accession number NM_002015.2, incorporated herein as SEQ ID NO:4). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human forkhead box O1A mRNA levels by quantitative real-time PCR as described in other examples herein. Data are averages from two experiments in which T-24 cells were treated with the antisense oligonucleotides of the present invention. The positive control for each datapoint is identified in the table by sequence ID number. If present, "N.D." indicates "no data".

TABLE 1

Inhibition of human forkhead box O1A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 188750 | 5'UTR | 4 | 4 | tgcctgttgaatgtggcggc | 65 | 18 | 2 |
| 188755 | Coding | 4 | 457 | ccggcctgggcagcggccag | 79 | 19 | 2 |
| 188757 | Coding | 4 | 701 | ccctggaagtccccgcacag | 77 | 20 | 2 |
| 188759 | Coding | 4 | 878 | ttggtgatgaggtcggcgta | 91 | 21 | 2 |
| 188761 | Coding | 4 | 889 | tctcgatggccttggtgatg | 80 | 22 | 2 |
| 188763 | Coding | 4 | 959 | ttgaagtagggcacgctctt | 72 | 23 | 2 |
| 188765 | Coding | 4 | 1092 | ctctggattgagcatccacc | 61 | 24 | 2 |
| 188766 | Coding | 4 | 1155 | aaatttactgttgttgtcca | 63 | 25 | 2 |
| 188767 | Coding | 4 | 1161 | cttagcaaatttactgttgt | 51 | 26 | 2 |
| 188769 | Coding | 4 | 1205 | ccagactggagagatgcttt | 69 | 27 | 2 |
| 188771 | Coding | 4 | 1304 | aatgtactccagttatcaaa | 58 | 28 | 2 |
| 188773 | Coding | 4 | 1510 | agagaaggttgagattatcc | 75 | 29 | 2 |
| 188774 | Coding | 4 | 1664 | gggctcatgctggattggcc | 63 | 30 | 2 |
| 188776 | Coding | 4 | 1782 | gggaggagagtcagaagtca | 0 | 31 | 2 |
| 188778 | Coding | 4 | 1904 | tgagatgcctggctgccata | 87 | 32 | 2 |
| 188780 | Coding | 4 | 1916 | atcattttgttatgagatgc | 75 | 33 | 2 |
| 188781 | Coding | 4 | 2091 | cagggcactcatctgcatgg | 74 | 34 | 2 |
| 188782 | Coding | 4 | 2126 | tagccattgcagctgctcac | 84 | 35 | 2 |
| 188783 | Coding | 4 | 2162 | gggagcttctcctggtggag | 27 | 36 | 2 |
| 188785 | Coding | 4 | 2176 | catccaagtcacttgggagc | 73 | 37 | 2 |
| 188787 | Coding | 4 | 2231 | aggtcattccgaatgatgga | 61 | 38 | 2 |
| 188789 | Coding | 4 | 2246 | gtatctccatccatgaggtc | 55 | 39 | 2 |
| 188790 | Coding | 4 | 2285 | ctttggttgggcaacacatt | 63 | 40 | 2 |
| 188791 | Coding | 4 | 2290 | ggaagctttggttgggcaac | 60 | 41 | 2 |
| 188793 | Coding | 4 | 2302 | tgacactgtgtgggaagctt | 85 | 42 | 2 |
| 188795 | 3'UTR | 4 | 2384 | tgctgtcagacaatctgaag | 62 | 43 | 2 |

TABLE 1-continued

Inhibition of human forkhead box O1A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 188797 | 3'UTR | 4 | 2575 | ggcacagtccttatctacag | 83 | 44 | 2 |
| 188799 | 3'UTR | 4 | 2605 | ttggcacttcattgtaatga | 76 | 45 | 2 |
| 188801 | 3'UTR | 4 | 2617 | ggtgtagtgagtttggcact | 72 | 46 | 2 |
| 188803 | 3'UTR | 4 | 2753 | aaagagtataaactttcctt | 64 | 47 | 2 |
| 188805 | 3'UTR | 4 | 3046 | tgtacaaatttgcaaataac | 76 | 48 | 2 |
| 188807 | 3'UTR | 4 | 3079 | catttatctggaaattagaa | 44 | 49 | 2 |
| 188809 | 3'UTR | 4 | 3163 | tagactctagttttaagaaa | 34 | 50 | 2 |
| 188811 | 3'UTR | 4 | 3174 | atgtaacaaagtagactcta | 76 | 51 | 2 |
| 188813 | 3'UTR | 4 | 3265 | taaaattagtactaatccag | 73 | 52 | 2 |
| 188815 | 3'UTR | 4 | 3467 | tgaaatttctttaaaataca | 0 | 53 | 2 |
| 188820 | 3'UTR | 4 | 4919 | aatcaaacaaggctgcatag | 57 | 54 | 2 |

As shown in Table 1, SEQ ID NOs 18, 19, 20, 21, 22, 23, 24, 25, 26, 27, 28, 29, 30, 32, 33, 34, 35, 37, 38, 39, 40, 41, 42, 43, 44, 45, 46, 47, 48, 51, 52 and 54 demonstrated at least 50% inhibition of human forkhead box O1A expression in this assay. SEQ ID NOs 21, 32, and 42 are particularly effective at inhibiting forkhead box O1A expression. The target sites to which these sequences are complementary are herein referred to as "target regions" and are suitable sites for targeting by compounds of the present invention. These target regions are shown in Table 3. The sequences represent the reverse complement of the compounds shown in Table 1. "Target site" indicates the first (5'-most) nucleotide number of the corresponding target nucleic acid. Also shown in Table 3 is the species in which each of the preferred target regions was found.

Example 18

Modulation of Mouse Forkhead Box O1A Expression by Chimeric Phosphorothioate Oligonucleotides Having 2'-MOE Wings and a Deoxy Gap In accordance with the present invention, a second series of oligonucleotides were designed to target different regions of the mouse forkhead box O1A RNA, using published sequences (GenBank accession number AJ252157.1, incorporated herein as SEQ ID NO:11, GenBank accession number BE198396.1, incorporated herein as SEQ ID NO:55, and the complement of GenBank accession number AA959612.1, incorporated herein as SEQ ID NO:56). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse forkhead box O1A mRNA levels by quantitative real-time PCR as described in other examples herein. Data are averages from two experiments in which b.END cells were treated with the antisense oligonucleotides of the present invention. The positive control for each datapoint is identified in the table by sequence ID number. If present, "N.D." indicates "no data".

TABLE 2

Inhibition of mouse forkhead box O1A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 188751 | 5'UTR | 11 | 61 | cgctgctgcctgttgaatgt | 29 | 58 | 1 |
| 188752 | 5'UTR | 11 | 223 | tgtctaaggagcctccgagt | 46 | 59 | 1 |
| 188753 | 5'UTR | 11 | 384 | cagagaagtaccgggagacg | 39 | 60 | 1 |
| 188754 | Start Codon | 11 | 419 | cttcggccatggtgccccg | 63 | 61 | 1 |

TABLE 2-continued

Inhibition of mouse forkhead box O1A mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 188756 | Coding | 11 | 506 | taaactccggcctgggcagc | 42 | 62 | 1 |
| 188758 | Coding | 11 | 889 | caggttgccccacgcgttgc | 67 | 63 | 1 |
| 188760 | Coding | 11 | 917 | tggccttggtgatgaggtcg | 17 | 64 | 1 |
| 188762 | Coding | 11 | 946 | ggtgagcctcttctcggctg | 54 | 65 | 1 |
| 188764 | Coding | 11 | 1096 | tccagttccttcattctgca | 77 | 66 | 1 |
| 188768 | Coding | 11 | 1201 | tcggctcttagcaaatttac | 32 | 67 | 1 |
| 188770 | Coding | 11 | 1332 | ctccagttatcaaagtcatc | 45 | 68 | 1 |
| 188772 | Coding | 11 | 1487 | acagactgggcagcgtagac | 36 | 69 | 1 |
| 188775 | Coding | 11 | 1704 | ggcaaagggctcatgctgga | 87 | 70 | 1 |
| 188777 | Coding | 11 | 1908 | accgaattagggcccatcat | 50 | 71 | 1 |
| 188779 | Coding | 11 | 1944 | ttgttatgagatgcctggct | 35 | 72 | 1 |
| 188784 | Coding | 11 | 2202 | tcacttgggagcttctcctg | 50 | 73 | 1 |
| 188786 | Coding | 11 | 2216 | acatgccatccaagtcactt | 32 | 74 | 1 |
| 188788 | Coding | 11 | 2271 | tccatgaggtcattccgaat | 59 | 75 | 1 |
| 188792 | Coding | 11 | 2330 | tgtgtgggaagctttggttg | 35 | 76 | 1 |
| 188794 | Stop Codon | 11 | 2377 | cactaactcttagcctgaca | 57 | 77 | 1 |
| 188796 | 3'UTR | 11 | 2424 | agttcctgctgtcagacaat | 43 | 78 | 1 |
| 188798 | 3'UTR | 11 | 2611 | ccaatggcacagtccttatc | 56 | 79 | 1 |
| 188800 | 3'UTR | 11 | 2640 | gtgagtttggcacttcattg | 50 | 80 | 1 |
| 188802 | 3'UTR | 11 | 2769 | ataaactttccttggaccaa | 72 | 81 | 1 |
| 188804 | 3'UTR | 11 | 3011 | agacctgtacaaagctggca | 69 | 82 | 1 |
| 188806 | 3'UTR | 11 | 3090 | tctggaaattagaaccattt | 38 | 83 | 1 |
| 188808 | 3'UTR | 11 | 3169 | ctagttttaagaaaacatta | 18 | 84 | 1 |
| 188810 | 3'UTR | 11 | 3181 | acaaagtagactctagtttt | 34 | 85 | 1 |
| 188812 | 3'UTR | 11 | 3272 | tagtactaatccagttagaa | 34 | 86 | 1 |
| 188814 | 3'UTR | 11 | 3363 | tgcaagtactaattacaatg | 33 | 87 | 1 |
| 188816 | 3'UTR | 11 | 3505 | tggtgctatgcgctgtacac | 54 | 88 | 1 |
| 188817 | 3'UTR | 11 | 3905 | agctggctggttttccaagtt | 58 | 89 | 1 |
| 188818 | 3'UTR | 11 | 4141 | ggccttctcataaaggcaaa | 47 | 90 | 1 |
| 188819 | 3'UTR | 11 | 4691 | agttcactgtgccccagaca | 68 | 91 | 1 |
| 188821 | 3'UTR | 11 | 4923 | gaaacaatacatctttatat | 26 | 92 | 1 |
| 188822 | 3'UTR | 55 | 131 | gactcagtttgtccaagcag | 68 | 93 | 1 |
| 188823 | 3'UTR | 55 | 413 | gtttggtttgcataaagcac | 51 | 94 | 1 |
| 188824 | 3'UTR | 55 | 423 | gggccaggctgtttggtttg | 2 | 95 | 1 |

TABLE 2-continued

Inhibition of mouse forkhead box O1A mRNA levels by chimeric phosphorothioate oligonucleotides having 2'-MOE wings and a deoxy gap

| ISIS # | TARGET REGION | TARGET SEQ ID NO | TARGET SITE | SEQUENCE | % INHIB | SEQ ID NO | CONTROL SEQ ID NO |
|---|---|---|---|---|---|---|---|
| 188825 | 3'UTR | 56 | 271 | ggcacttctcagatagcaat | 67 | 96 | 1 |
| 188826 | 3'UTR | 56 | 351 | gaggatttatgtacatttat | 0 | 97 | 1 |

As shown in Table 2, SEQ ID NOs 59, 60, 61, 62, 63, 65, 66, 68, 69, 70, 71, 72, 73, 75, 76, 77, 78, 79, 80, 81, 82, 83, 88, 89, 90, 91, 93, 94 and 96 demonstrated at least 35% inhibition of mouse forkhead box O1A expression in this experiment. Compounds having SEQ ID Nos 66 70, and 81 (compounds 188764, 188775, and 188802) are particularly effective at inhibiting forkhead box O1A expression. The target sites to which these preferred sequences are complementary are herein referred to as "target regions" and are suitable sites for targeting by compounds of the present invention. These target regions are shown in Table 3. The sequences represent the reverse complement of the preferred antisense compounds shown in Table 1. "Target site" indicates the first (5'-most) nucleotide number of the corresponding target nucleic acid. Also shown in Table 3 is the species in which each of the target regions was found.

TABLE 3

Sequence and position of preferred target regions identified in forkhead box O1A.

| SITE ID | TARGET SEQ ID NO | TARGET SITE | SEQUENCE | REV COMP OF SEQ ID | ACTIVE IN | SEQ ID NO |
|---|---|---|---|---|---|---|
| 104287 | 4 | 4 | gccgccacattcaacaggca | 18 | H. sapiens | 98 |
| 104292 | 4 | 457 | ctggccgctgcccaggccgg | 19 | H. sapiens | 99 |
| 104294 | 4 | 701 | ctgtgcggggacttccaggg | 20 | H. sapiens | 100 |
| 104296 | 4 | 878 | tacgccgacctcatcaccaa | 21 | H. sapiens | 101 |
| 104298 | 4 | 889 | catcaccaaggccatcgaga | 22 | H. sapiens | 102 |
| 104300 | 4 | 959 | aagagcgtgccctacttcaa | 23 | H. sapiens | 103 |
| 104302 | 4 | 1092 | ggtggatgctcaatccagag | 24 | H. sapiens | 104 |
| 104303 | 4 | 1155 | tggacaacaacagtaaattt | 25 | H. sapiens | 105 |
| 104304 | 4 | 1161 | acaacagtaaatttgctaag | 26 | H. sapiens | 106 |
| 104306 | 4 | 1205 | aaagcatctctccagtctgg | 27 | H. sapiens | 107 |
| 104308 | 4 | 1304 | tttgataactggagtacatt | 28 | H. sapiens | 108 |
| 104310 | 4 | 1510 | ggataatctcaaccttctct | 29 | H. sapiens | 109 |
| 104311 | 4 | 1664 | ggccaatccagcatgagccc | 30 | H. sapiens | 110 |
| 104315 | 4 | 1904 | tatggcagccaggcatctca | 32 | H. sapiens | 111 |
| 104317 | 4 | 1916 | gcatctcataacaaaatgat | 33 | H. sapiens | 112 |
| 104318 | 4 | 2091 | ccatgcagatgagtgccctg | 34 | H. sapiens | 113 |
| 104319 | 4 | 2126 | gtgagcagctgcaatggcta | 35 | H. sapiens | 114 |
| 104322 | 4 | 2176 | gctcccaagtgacttggatg | 37 | H. sapiens | 115 |
| 104324 | 4 | 2231 | tccatcattcggaatgacct | 38 | H. sapiens | 116 |
| 104326 | 4 | 2246 | gacctcatggatggagatac | 39 | H. sapiens | 117 |
| 104327 | 4 | 2285 | aatgtgttgcccaaccaaag | 40 | H. sapiens | 118 |
| 104328 | 4 | 2290 | gttgcccaaccaaagcttcc | 41 | H. sapiens | 119 |
| 104330 | 4 | 2302 | aagcttcccacacagtgtca | 42 | H. sapiens | 120 |
| 104332 | 4 | 2384 | cttcagattgtctgacagca | 43 | H. sapiens | 121 |

TABLE 3-continued

Sequence and position of preferred target regions identified in forkhead box O1A.

| SITE ID | TARGET SEQ ID NO | TARGET SITE | SEQUENCE | REV COMP OF SEQ ID | ACTIVE IN | SEQ ID NO |
|---|---|---|---|---|---|---|
| 104334 | 4 | 2575 | ctgtagataaggactgtgcc | 44 | H. sapiens | 122 |
| 104336 | 4 | 2605 | tcattacaatgaagtgccaa | 45 | H. sapiens | 123 |
| 104338 | 4 | 2617 | agtgccaaactcactacacc | 46 | H. sapiens | 124 |
| 104340 | 4 | 2753 | aaggaaagtttatactcttt | 47 | H. sapiens | 125 |
| 104342 | 4 | 3046 | gttatttgcaaatttgtaca | 48 | H. sapiens | 126 |
| 104348 | 4 | 3174 | tagagtctactttgttacat | 51 | H. sapiens | 127 |
| 104350 | 4 | 3265 | ctggattagtactaatttta | 52 | H. sapiens | 128 |
| 104357 | 4 | 4919 | ctatgcagccttgtttgatt | 54 | H. sapiens | 129 |
| 104289 | 11 | 223 | actcggaggctccttagaca | 59 | M. musculus | 130 |
| 104290 | 11 | 384 | cgtctcccggtacttctctg | 60 | M. musculus | 131 |
| 104291 | 11 | 419 | cgggggcaccatggccgaag | 61 | M. musculus | 132 |
| 104293 | 11 | 506 | gctgcccaggccggagttta | 62 | M. musculus | 133 |
| 104295 | 11 | 889 | gcaacgcgtggggcaacctg | 63 | M. musculus | 134 |
| 104299 | 11 | 946 | cagccgagaagaggctcacc | 65 | M. musculus | 135 |
| 104301 | 11 | 1096 | tgcagaatgaaggaactgga | 66 | M. musculus | 136 |
| 104307 | 11 | 1332 | gatgactttgataactggag | 68 | M. musculus | 137 |
| 104309 | 11 | 1487 | gtctacgctgcccagtctgt | 69 | M. musculus | 138 |
| 104312 | 11 | 1704 | tccagcatgagccctttgcc | 70 | M. musculus | 139 |
| 104314 | 11 | 1908 | atgatgggccctaattcggt | 71 | M. musculus | 140 |
| 104316 | 11 | 1944 | agccaggcatctcataacaa | 72 | M. musculus | 141 |
| 104321 | 11 | 2202 | caggagaagctcccaagtga | 73 | M. musculus | 142 |
| 104325 | 11 | 2271 | attcggaatgacctcatgga | 75 | M. musculus | 143 |
| 104329 | 11 | 2330 | caaccaaagcttcccacaca | 76 | M. musculus | 144 |
| 104331 | 11 | 2377 | tgtcaggctaagagttagtg | 77 | M. musculus | 145 |
| 104333 | 11 | 2424 | attgtctgacagcaggaact | 78 | M. musculus | 146 |
| 104335 | 11 | 2611 | gataaggactgtgccattgg | 79 | M. musculus | 147 |
| 104337 | 11 | 2640 | caatgaagtgccaaactcac | 80 | M. musculus | 148 |
| 104339 | 11 | 2769 | ttggtccaaggaaagtttat | 81 | M. musculus | 149 |
| 104341 | 11 | 3011 | tgccagctttgtacaggtct | 82 | M. musculus | 150 |
| 104343 | 11 | 3090 | aaatggttctaatttccaga | 83 | M. musculus | 151 |
| 104353 | 11 | 3505 | gtgtacagcgcatagcacca | 88 | M. musculus | 152 |
| 104354 | 11 | 3905 | aacttggaaaccagccagct | 89 | M. musculus | 153 |
| 104355 | 11 | 4141 | tttgcctttatgagaaggcc | 90 | M. musculus | 154 |
| 104356 | 11 | 4691 | tgtctggggcacagtgaact | 91 | M. musculus | 155 |
| 104359 | 55 | 131 | ctgcttggacaaactgagtc | 93 | M. musculus | 156 |

TABLE 3-continued

Sequence and position of preferred target
regions identified in forkhead box O1A.

| SITE ID | TARGET SEQ ID NO | TARGET SITE | SEQUENCE | REV COMP OF SEQ ID | ACTIVE IN | SEQ ID NO |
|---|---|---|---|---|---|---|
| 104360 | 55 | 413 | gtgctttatgcaaaccaaac | 94 | M. musculus | 157 |
| 104362 | 56 | 271 | attgctatctgagaagtgcc | 96 | M. musculus | 158 |

As these "target regions" have been found by experimentation to be open to, and accessible for, hybridization with the compounds of the present invention, one of skill in the art will recognize or be able to ascertain, using no more than routine experimentation, further embodiments of the invention that encompass other compounds that specifically hybridize to these sites and consequently inhibit the expression of forkhead box O1A.

In one embodiment, the "target region" may be employed in screening candidate antisense compounds. "Candidate" compounds are those that inhibit the expression of a nucleic acid molecule encoding forkhead box O1A and which comprise at least an 8-nucleobase portion which is complementary to a target region. The method comprises the steps of contacting a target region of a nucleic acid molecule encoding forkhead box O1A with one or more candidate compounds, and selecting for one or more candidate antisense compounds which inhibit the expression of a nucleic acid molecule encoding forkhead box O1A. Once it is shown that the candidate compound or compounds are capable of inhibiting the expression of a nucleic acid molecule encoding forkhead box O1A, the candidate compound may be employed as a compound in accordance with the present invention.

According to the present invention, compounds include ribozymes, external guide sequence (EGS) oligonucleotides (oligozymes), and other short catalytic RNAs or catalytic oligonucleotides which hybridize to the target nucleic acid and modulate its expression.

Example 19

Western Blot Analysis of Forkhead Box O1A Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to forkhead box O1A is used, with a radiolabeled or fluorescently labeled secondary antibody directed against the primary antibody species. Bands are visualized using a PHOSPHORIMAGER™ (Molecular Dynamics, Sunnyvale Calif.).

Example 20

In Vitro Modulation of Forkhead Box O1A

Using the methods described in Example 15, a dose-dependent reduction of forkhead box O1A mRNA and protein was achieved with compound 188764 in primary murine hapatocytes.

In another experiment, compounds 188764, 188781, and 188802 resulted in a dose-dependent reduction in forkhead box O1A mRNA (expressed as % no treatment) (see Table 4).

TABLE 4

| Concentration | Compound 188764 | Compound 188781 | Compound 188802 |
|---|---|---|---|
| 1 nM | 65% | 62 | 60 |
| 10 nM | 38 | 58 | 62 |
| 50 nM | 18 | 48 | 55 |
| 100 nM | 8 | 23 | 45 |
| 150 nM | 10 | 23 | 30 |

Example 21

Four Week Lean Mouse Model

C57B16 (normal lean) mice were used in this 4 week lean mouse screen. These mice are commercially available through any vendor, such as Jackson Laboratories or Charles River, and are considered to be normal. The term "lean" is used to contrast these mice to obese db/db mice. Several compounds including 188775, 188793, 188764, 188802, and 141923 (a scramble sequence used as a control—it does not bind to forkhead box O1A) were administered to C57B16 mice to determine the effect on forkhead expression. Forkhead box O1A mRNA expression was found to be reduced in both liver and fat using the procedures described in the earlier examples. Compound 188802, 188793, and 188764 resulted in the greatest amount of reduction of forkhead box O1A mRNA expression.

In another experiment, administering compound 188764 resulted in a decrease in liver forkhead box O1A mRNA (40%) and protein (45%) (same study design as the previous one 4 weeks treatment).

In another experiment were C57B16 mice were treated for 2 weeks, compounds 188764, 188781, and 188802 resulted in a decrease in forkhead box O1A mRNA in liver (results expressed as % of saline control) (compound 188764=50%; compound 188781=79%; compound 188802=70%).

Figure 2:
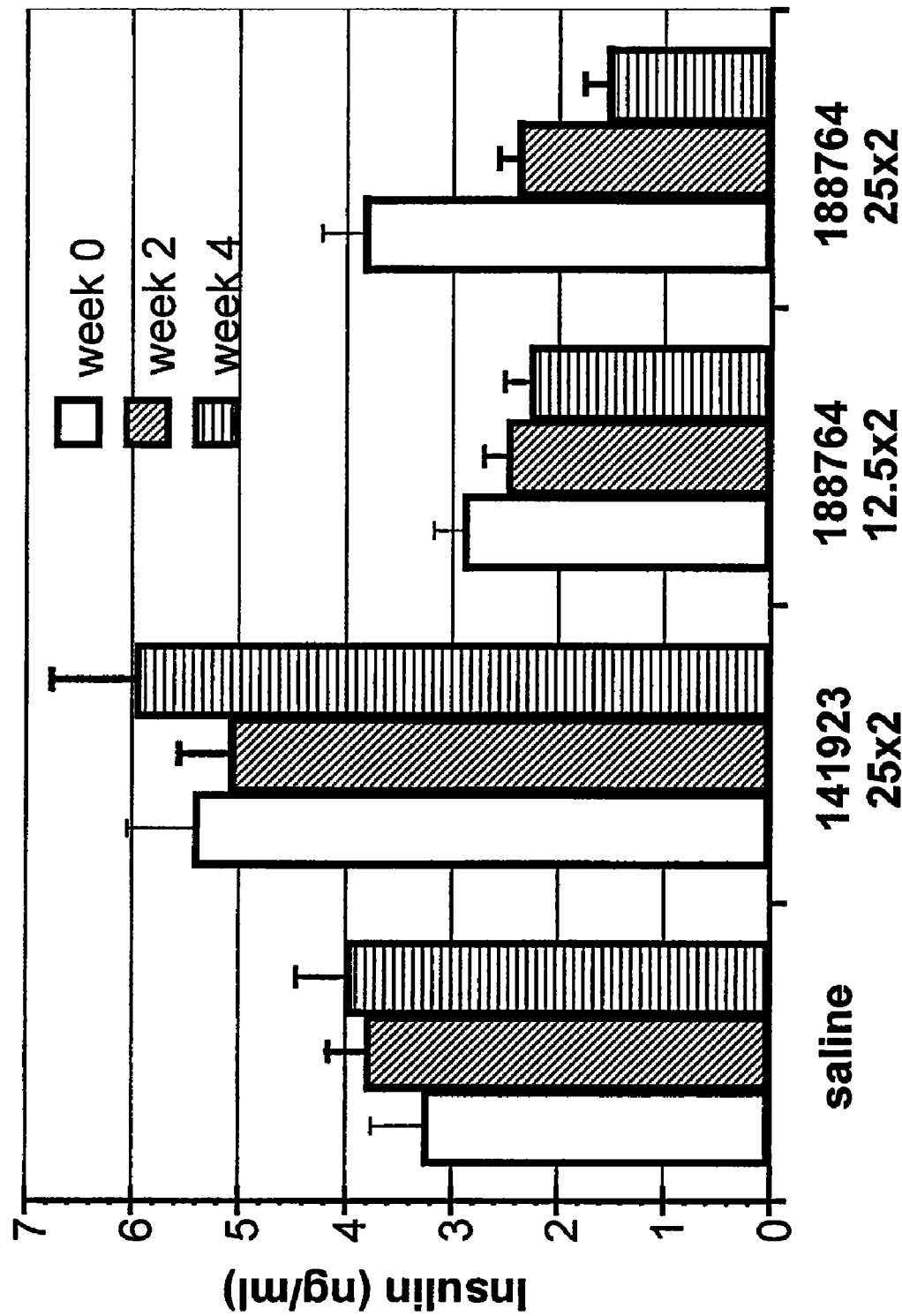
FIG. 2 shows the effects of an antisense compound on insulin levels in lean C57B16 mice. Compound 188764 decreased insulin levels by more than 50% at the highest dose.

In another experiment, C57B16 lean mice were treated with Compounds 188764 (12.5 and 25 mg/kg×2 weekly), or 141923 (25 mg/kg×2 weekly), or saline for 4 weeks. Plasma glucose and lipid levels were measured every other week (at 0, 2, and 4 weeks). At week 3, mice were fasted for 12 hours and a glucose tolerance test was performed (glucose tolerance test measures the body's ability to metabolize glucose). At the $4^{th}$ week, the mice were sacrificed and liver, fat, muscle, kidneys, pancreas, and bone marrow were collected. Compound 188764 significantly improved the glucose tolerance test at 12.5 and 25 (2) mg/kg/week (FIG. 1) and decreased insulin levels by more than 50% at the highest dose (FIG. 2).

Example 22 db/db Mouse Model

The db/db diabetic mouse model was used in this screen to further examine compound 188764 in regard to fed and fasted blood glucose and monitored at 0, 2, and 4 weeks. The db/db mice are commercially available from The Jackson Laboratory JAX® GEMM® Strain—Spontaneous Mutation Congenic Mice, and are homozygous for the diabetes spontaneous mutation (Lepr$^{db}$). These mice become identifiably obese around 3 to 4 weeks of age. db/db mice at 9 weeks of age were injected twice a week with saline or compound 188764 for 4 weeks. Blood glucose was measured every other week. In one experiment, mice were fasted for 10, 12, and 16 hours and blood glucose was measured at the end of the fourth week. Fed plasma glucose levels were improved with compound 188764 and fasted blood glucose levels were also improved (results expressed as blood glucose mg/dl) (saline=about 220 at 10 hour fast, about 290 at 12 hours fast, and about 160 at 16 hours fast; compound 188764=about 170 at 10 hour fast, about 125 at 12 hours fast, and about 100 at 16 hours fast). Forkhead box O1A mRNA expression was reduced in both liver and fat. Fed blood glucose was consistently decreased by compound 188764 treatment at the highest dose by 100 mg/dl compared to fed blood glucose from saline and 141923 treated groups.

In another experiment, compound 188764 decreased blood glucose in the fasted and fed state.

Figure 3:
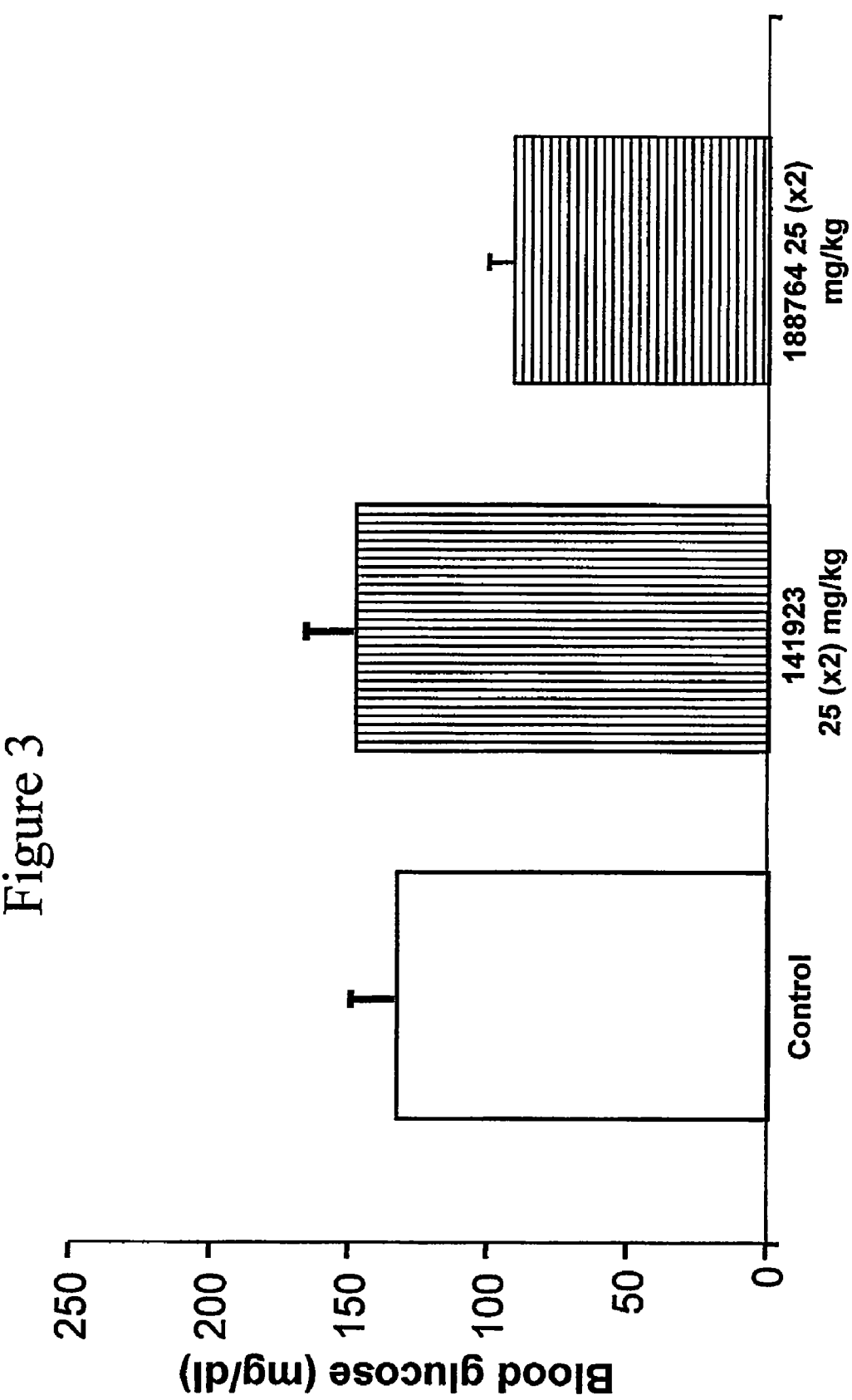
FIG. 3 shows the effects of an antisense compound on blood glucose after a 16 hour fast in 9-12 week old db/db mice. Compound 188764 significantly reduced blood glucose levels after a 16 hour fast in 9-12 weeks db/db mice.

In another experiment, compound 188764 significantly reduced blood glucose levels after a 16 hour fast in 9-12 weeks db/db mice (see, FIG. 3).

In another experiment, compound 188764 resulted in a decrease in forkhead box O1A mRNA and protein in liver and fat between 60-80%.

Example 23

High Fat Diet (HFD) Mouse Model

C57Bl6 mice fed with a high fat diet (high fat diet (HFD) induced diabetes after about 12 weeks of feeding) was used in this screen to further examine compound 188764 in regard to a glucose tolerance test and insulin tolerance test (insulin tolerance test assesses insulin sensitivity/presence of insulin resistance, as described in Black, *Metabolism*, 1998, 47, 1354-1359). C57Bl6 mice show high susceptibility to development of moderate obesity, hyper-glycemia, and insulin resistance when fed a high fat diet. In general, HFD fed mice were at 3 weeks of age started with HFD for 12 weeks and injected twice a week with saline or compounds for 4 weeks. Blood glucose was measured every other week, and plasma glucose and lipid levels were measured every other even week. At week 3, a glucose tolerance test was initiated in which 45 mice were fasted for 12 hours and given 2 g/kg glucose. Also at week 3, an insulin tolerance test was initiated in which another 45 mice were fasted for 4 hours and given 0.5 U/kg insulin. Compound 188764 was fed at 10, 25, and 50 mg/kg/wk.

Forkhead box O1A mRNA and protein expression was reduced in both liver (between 40-60%) and fat. Compound 188764 decreased plasma glucose levels in a dose-dependent manner. An improvement in the glucose tolerance test was observed with the feeding regimens of 25 and 50 mg/kg/wk of compound 188764 when compared to saline. Compound 188764 decreased fed and fasted (4 hour fast) plasma blood glucose levels. In addition, a dose response was achieved with compound 188764 with respect to lowering insulin levels (>90% at highest dose). No significant changes were observed in plasma cholesterol, plasma triglycerides, body weight, or ALT/AST (serum activities of alanine and aspartate aminotransferase, respectively) concentrations. Body weights were also unaffected by compound 188764.

Figure 4:
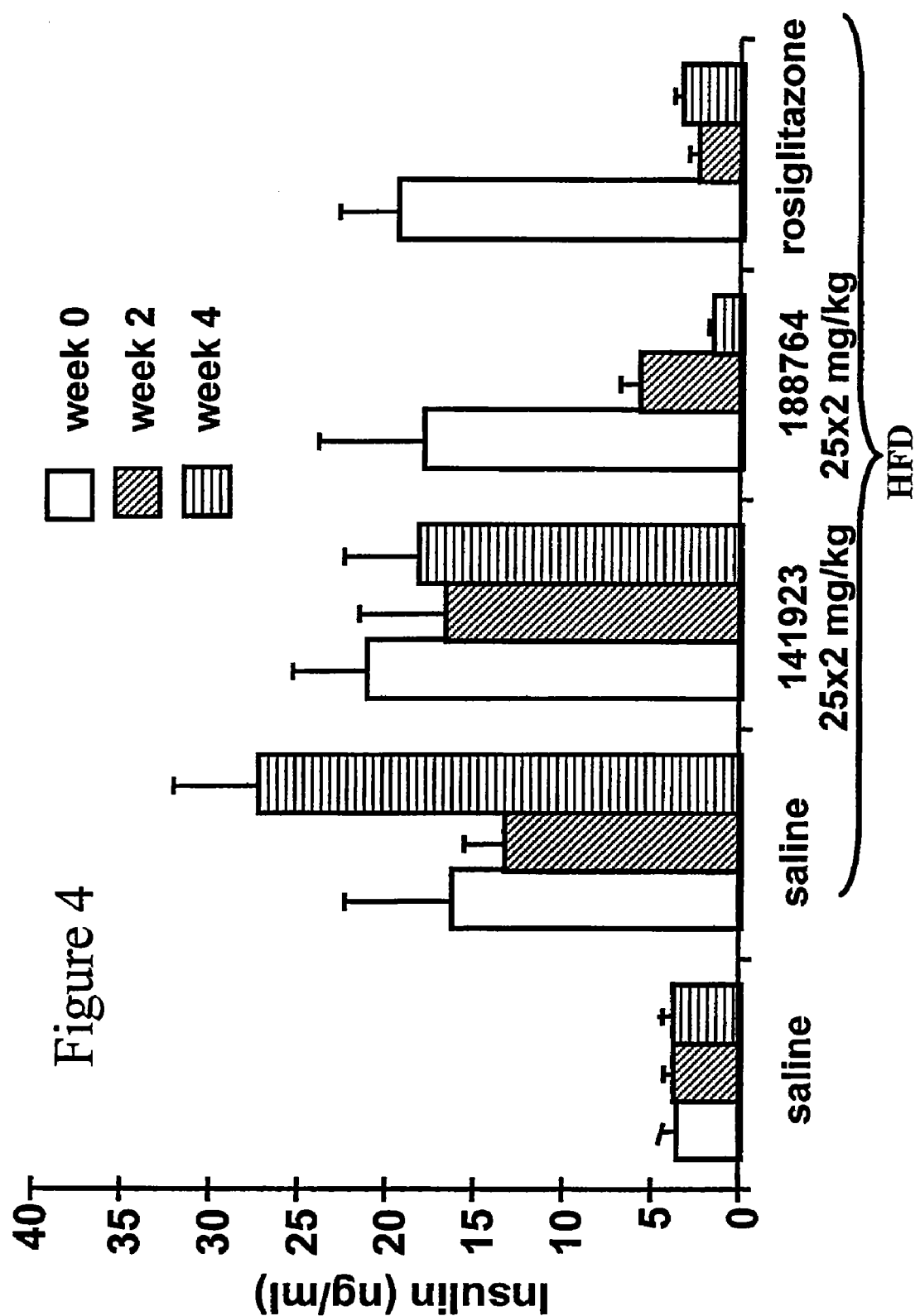
FIG. 4 shows the effects of an antisense compound on plasma insulin levels in high fat diet C57B16 mice. Compound 188764 and rosiglitazone decreased plasma insulin levels in high fat diet fed mice.

In another experiment, compound 188764 decreased blood glucose in the fed (18%) and fasted states, normalized glucose intolerance, normalized insulin levels (decreased by 94%). Compound 188764 (25×2 mg/kg) and rosiglitazone (rosiglitazone is a thiazolidinedione, the peroxisome proliferator-activated receptor-gamma agonists, which work by reducing the body's resistance to the action of insulin; used as a refernce compound) had similar effects on plasma insulin levels in HFD fed mice (see FIG. 4).

In another experiment, compound 188764 resulted in a decrease in forkhead box O1A mRNA and protein expression in liver and fat between 40-80%, and normalized glucose and insulin levels (decreased insulin levels greater than about 90%).

Figure 5:
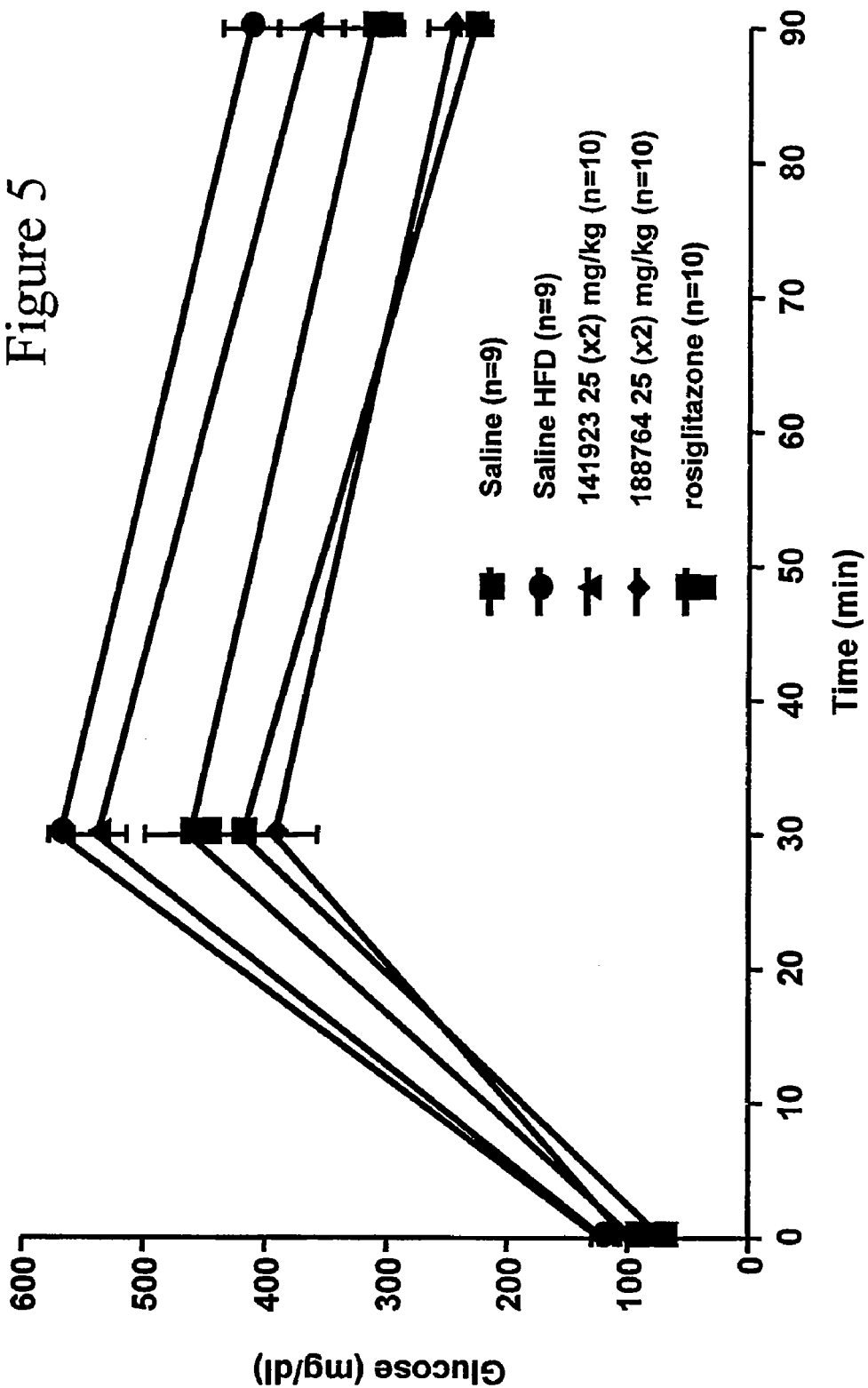
FIG. 5 shows effects of an antisense compound in a glucose tolerance test in high fat fed C57B16 mice. Compound 188764 normalized insulin levels in these animals.

Exemplary effects of Compound 188764 and rosiglitazone on a glucose tolerance test in high fat fed mice is shown in FIG. 5.

Example 24

Modulation of Human Forkhead O1A Expression

HEPG2 cells were treated with 50 nM compound for 20 hours. mRNA was analyzed by RT-PCR (TaqMan 7700), n=3. Results are shown below as the IC$_{50}$. Modulation of forkhead box O1A expression was correlated to modulation of glucose-6-phosphate expression for compounds 289841 and 289865. Table 5 lists several compounds targeted to human forkhead box O1A.

TABLE 5

| Compound # | Sequence | IC$_{50}$ Human HepG2 (nM) | SEQ ID NO: |
|---|---|---|---|
| 289800 | tgccccacgcgttgcggcgg | 20 | 159 |
| 289865 | ggcaacgtgaacaggtccaa | 15 | 160 |
| 289875 | agctgactatgtaacaaagt | 24 | 161 |
| 289813 | aactgtgatccagggctgtc | 25 | 162 |
| 289839 | cccagggcactcatctgcat | 25 | 163 |
| 289841 | ctaagcgctcaatgaacatg | 25 | 164 |
| 289866 | tagcagattgataacaggct | 25 | 165 |
| 289826 | ggctgggtgaattcaaactg | 30 | 166 |
| 188793 | tgacactgtgtgggaagctt | 30 | 42 |
| 289834 | catgaccgaattagggccca | 35 | 167 |
| 289842 | cattccgaatgatggattcc | 40 | 168 |
| 188790 | ctttggttgggcaacacatt | 38 | 40 |
| 188812 | tagtactaatccagttagaa | 25 | 86 |

Example 25

Modulation of Monkey Forkhead O1A Expression

Monkey primary hepatocytes were treated with 50 nM of antisense compounds for 20 hours. Levels of mRNA were analyzed by RT-PCR (TaqMan 7700). The results are shown in Table 6.

TABLE 6

| Compound # | Sequence | Monkey Hepatocyte IC$_{50}$ (nM) | SEQ ID NO: |
|---|---|---|---|
| 327652 | gctttggttgggcaacacat | 20 | 172 |
| 327612 | ccgcttctccgccgagctct | 18 | 173 |
| 327643 | ccgccagggcactcatctgc | 15 | 174 |
| 327658 | tgcttctctcagttcctgct | 19 | 175 |
| 327623 | catagaatgcacatcccctt | 24 | 176 |

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

---

What is claimed:

1. A compound comprising a modified oligonucleotide consisting of 8 to 80 linked nucleosides targeted to a nucleic acid molecule encoding forkhead box O1A, wherein said compound is at least 98% complementary to a nucleic acid molecule encoding forkhead box O1A (SEQ ID NO: 4) and inhibits the expression of forkhead box O1A, wherein the modified oligonucleotide is a chimeric oligonucleotide.

2. The compound of claim 1, wherein the modified oligonucleotide consists of 8 to 50 linked nucleosides.

3. The compound of claim 1, wherein the modified oligonucleotide consists of 12 to 30 linked nucleosides.

4. The compound of claim 1, wherein the modified oligonucleotide is a single-stranded oligonucleotide.

5. The compound of claim 1, wherein the modified oligonucleotide is a DNA oligonucleotide.

6. The compound of claim 1, wherein the modified oligonucleotide is an RNA oligonucleotide.

7. The compound of claim 1 wherein at least a portion of the modified oligonucleotide hybridizes with RNA to form an oligonucleotide-RNA duplex.

8. The compound of claim 1 wherein the modified oligonucleotide comprises at least one modified internucleoside linkage.

9. The compound of claim 8 wherein the modified internucleoside linkage is a phosphorothioate linkage.

10. The compound of claim 1, wherein at least one nucleoside comprises a modified sugar.

11. The compound of claim 10, wherein at least one modified sugar is a bicyclic sugar.

12. The compound of claim 10, wherein at least one modified sugar comprises a 2'-O-methoxyethyl.

13. The compound of claim 1, wherein at least one nucleoside comprises a modified nucleobase.

14. The compound of claim 13, wherein the modified nucleobase is a 5-methylcytosine.

15. A composition comprising the compound of claim 1 and a pharmaceutically acceptable carrier or diluent.

16. The compound of claim 1, wherein the modified oligonucleotide consists of 20 linked nucleosides.

17. The compound of claim 1, wherein the nucleobase sequence of the modified oligonucleotide is 99% complementary within SEQ ID NO: 4.

18. The compound of claim 1, wherein the nucleobase sequence of the modified oligonucleotide is 100% complementary within SEQ ID NO: 4.

19. A composition comprising a modified oligonucleotide consisting of 8 to 80 linked nucleosides and having a nucleobase sequence with 80% complementarity to a nucleic acid molecule encoding forkhead box O1A(SEQ ID NO: 4) and comprising at least 8 contiguous nucleobases of a nucleobase sequence selected from a sequence recited in any one of SEQ ID NOs: 18, 19, 20, 21, 22, 23, 24, 25, 26, 27, 28, 29, 30, 32, 33, 34, 35, 37, 38, 39, 40, 41, 42, 43, 44, 45, 46, 47, 48, 51, 52, 54, 86, 159, 160, 161, 162, 163, 164, 165, 166, 167, 168, 172, 173, 174, 175, and 176 or a salt thereof and a pharmaceutically acceptable carrier or diluent.

* * * * *